(12) United States Patent
Graham et al.

(10) Patent No.: US 8,608,783 B2
(45) Date of Patent: Dec. 17, 2013

(54) BONE PLATE WITH FLANGE MEMBER AND METHODS OF USE THEREOF

(75) Inventors: Thomas James Graham, Timonium, MD (US); Louise M. Focht, Del Mar, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 858 days.

(21) Appl. No.: 12/117,686

(22) Filed: May 8, 2008

(65) Prior Publication Data

US 2011/0106081 A1    May 5, 2011

(51) Int. Cl.
*A61B 17/80* (2006.01)

(52) U.S. Cl.
USPC ............... 606/280; 70/282; 70/286; 70/297

(58) Field of Classification Search
USPC ............. 606/61, 69–75, 280–299; 623/11.11, 623/16.11
See application file for complete search history.

(56) References Cited

U.S. PATENT DOCUMENTS

| 565,255 | A | | 8/1896 | Belden |
|---|---|---|---|---|
| 583,455 | A | | 6/1897 | Bush |
| 1,608,790 | A | | 11/1926 | Henslow |
| 2,031,483 | A | | 2/1936 | Interrante |
| 2,031,484 | A | | 2/1936 | Interrante |
| 3,939,828 | A | | 2/1976 | Mohr et al. |
| 4,206,517 | A | * | 6/1980 | Pappas et al. ............. 623/20.13 |
| 4,409,970 | A | | 10/1983 | Carrel |
| 4,658,822 | A | | 4/1987 | Kees, Jr. |
| 4,838,254 | A | | 6/1989 | Gauthier |
| 4,852,559 | A | | 8/1989 | Chernoff |
| 5,006,120 | A | | 4/1991 | Carter |
| 5,013,314 | A | | 5/1991 | Firica et al. |
| 5,092,889 | A | | 3/1992 | Campbell, Jr. |
| 5,312,426 | A | | 5/1994 | Segawa et al. |
| 5,372,604 | A | | 12/1994 | Trott |
| 5,374,268 | A | | 12/1994 | Sander |
| 5,441,509 | A | | 8/1995 | Vidal et al. |
| 5,487,741 | A | * | 1/1996 | Maruyama et al. ............. 606/60 |
| 5,487,746 | A | | 1/1996 | Yu et al. |
| 5,507,747 | A | | 4/1996 | Yuan et al. |
| 5,586,985 | A | | 12/1996 | Putnam et al. |
| 5,709,682 | A | | 1/1998 | Medoff |
| 5,718,704 | A | | 2/1998 | Medoff |
| 5,931,839 | A | | 8/1999 | Medoff |
| 5,935,128 | A | | 8/1999 | Carter et al. |
| 5,941,878 | A | * | 8/1999 | Medoff ........................... 606/60 |
| 6,060,641 | A | * | 5/2000 | Manolidis ..................... 128/898 |
| 6,066,141 | A | | 5/2000 | Dall et al. |
| 6,077,266 | A | | 6/2000 | Medoff |
| 6,113,603 | A | | 9/2000 | Medoff |
| 6,248,109 | B1 | | 6/2001 | Stoffella |
| 6,302,884 | B1 | | 10/2001 | Wellisz et al. |
| 6,302,887 | B1 | | 10/2001 | Spranza et al. |

(Continued)

*Primary Examiner* — Sameh Boles
*Assistant Examiner* — Samuel Hanna
(74) *Attorney, Agent, or Firm* — Tarolli, Sundheim, Covell & Tummino LLP

(57) ABSTRACT

Aspects of the present disclosure include a bone plate and/or a bone plate system. The bone plate includes an elongate body, which elongate body includes a top and a bottom surface as well as a distal portion, a proximal portion, and an intercalating portion disposed between the distal and proximal portions. The elongate body also includes a flange member, which flange member is configured for contacting a bone portion, e.g., a fractured bone portion, so as to aid in the stabilization and correct anatomical reduction thereof.

1 Claim, 10 Drawing Sheets

(56) References Cited

U.S. PATENT DOCUMENTS

| | | |
|---|---|---|
| 6,440,135 B2 | 8/2002 | Orbay et al. |
| 6,464,710 B1 | 10/2002 | Foster |
| 6,511,482 B1 * | 1/2003 | Wellisz et al. ................. 606/281 |
| 6,554,835 B1 | 4/2003 | Lee |
| 6,652,530 B2 | 11/2003 | Ip et al. |
| 6,923,812 B1 * | 8/2005 | Wellisz ............................ 606/75 |
| 7,037,308 B2 | 5/2006 | Medoff |
| 7,090,676 B2 | 8/2006 | Huebner et al. |
| 7,189,237 B2 | 3/2007 | Huebner |
| 7,229,445 B2 | 6/2007 | Hayeck et al. |
| 7,235,079 B2 | 6/2007 | Jensen et al. |
| 7,250,053 B2 | 7/2007 | Orbay |
| 7,316,687 B2 | 1/2008 | Aikins et al. |
| 7,326,212 B2 | 2/2008 | Huebner |
| 2002/0095157 A1 | 7/2002 | Bowman |
| 2002/0143339 A1 | 10/2002 | Medoff |
| 2002/0147452 A1 | 10/2002 | Medoff et al. |
| 2003/0100898 A1 * | 5/2003 | Wellisz ............................ 606/69 |
| 2003/0100902 A1 * | 5/2003 | Wellisz et al. .................. 606/72 |
| 2004/0030388 A1 * | 2/2004 | Null et al. .................. 623/17.11 |
| 2004/0102778 A1 * | 5/2004 | Huebner et al. ................ 606/71 |
| 2004/0158251 A1 | 8/2004 | Morrison et al. |
| 2004/0230312 A1 | 11/2004 | Hanson et al. |
| 2005/0070902 A1 | 3/2005 | Medoff |
| 2005/0154392 A1 | 7/2005 | Medoff et al. |
| 2005/0234458 A1 | 10/2005 | Huebner |
| 2005/0245931 A1 | 11/2005 | Orbay |
| 2005/0251138 A1 * | 11/2005 | Boris et al. ..................... 606/61 |
| 2006/0015101 A1 | 1/2006 | Warburton et al. |
| 2006/0089648 A1 | 4/2006 | Masini |
| 2006/0155284 A1 | 7/2006 | Doherty et al. |
| 2006/0173458 A1 | 8/2006 | Forstein et al. |
| 2006/0189992 A1 | 8/2006 | Medoff |
| 2006/0235404 A1 * | 10/2006 | Orbay et al. .................... 606/69 |
| 2006/0241612 A1 | 10/2006 | Medoff |
| 2007/0118126 A1 | 5/2007 | Medoff et al. |
| 2007/0123880 A1 | 5/2007 | Medoff |
| 2007/0173841 A1 | 7/2007 | Ralph et al. |
| 2009/0043310 A1 | 2/2009 | Rasmussen |

* cited by examiner

BONE PLATE WITH FLANGE MEMBER AND METHODS OF USE THEREOF

BACKGROUND

A bone fracture is a condition of a bone in which at least a portion of the bone has cracked, broken, and or fragmented. Bone fractures can be caused in several different ways, for instance, as a result of a high force impact, stress, or as the result of conditions that presuppose the bones for fracturing, such as osteoporosis, cancer, and the like. Fractures may be closed or compound and they may be simple or multi-fragmentary, e.g., comminuted.

The ease and success of treatment of bone fractures often depends on the type and location of the fracture and the tools available for correcting the crack, break, and/or fragmentation of the bone to be treated. For instance, a closed, simple fracture along a diaphyseal portion of a long bone may be relatively simple to correct and therefore treat. However, a distal radius fracture due to its location and the morphology of the bones involved, may be difficult to correct and treat.

There are several methods for treating bone fractures, all of which typically involve the stabilization of the bone fragments. For instance, the fractured bone pieces may be reduced, e.g., aligned, and restored to their natural position, which position is then maintained using standard immobilization techniques, such as using plaster or fiberglass casts, as well as implanting surgical nails, screws, plates, and wires which function to fix and hold the fractured bone together.

However, the use of casts and typical surgical nails, screws, plates, and wires for the treatment of fractured bones have several drawbacks. For example, casts are problematic in that they are big, bulky and usually only allow a small degree of motion of associated joints. Further, casts often fail to provide adequate internal fixation, thus, resulting in pain, deformity, and/or prolonged disability. Additionally, the use of typical nails, screws, plates, and wires can be problematic because these devices may be hard to apply, are not easily manipulated so as to appropriately reduce and fix the bone in correct alignment, and are not suited for reducing fragments, e.g. multiple fracture portions, that are displaced from the main loci of the fracture, often requiring additionally plating and/or wiring.

The details of one or more variations of the subject matter described herein are set forth in the description below and the accompanying drawings. Other features and advantages of the subject matter described herein will be apparent from the description and drawings, and from the claims.

SUMMARY

Aspects of the present disclosure include a bone plate and/or a bone plate system. The bone plate includes an elongate body, which elongate body includes a top and a bottom surface as well as a proximal portion, a distal portion, and an intercalating portion disposed between the proximal and distal portions. The elongate body also includes a flange member, which flange member is configured for contacting a bone portion, e.g., a fractured bone portion, so as to aid in the stabilization and correct anatomical reduction thereof.

The flange member includes a top and a bottom surface as well as a connector, which connector joins the top surface of the flange member with the bottom surface of the elongated body. The flange member may be joined with the elongate body at the proximal, intercalating, or distal portion. Further, in some variations, the proximal portion may additionally be configured for engaging one or more of a bone portion and a second bone plate, such as peri-articular extension plate.

Accordingly, in certain aspects, the present disclosure is directed to a bone plate system, which system may include at least a first bone plate, such as a primary bone plate having flange member extending there from, as described above, and a second bone plate. The first and second bone plates of the system may be affixed to one or more bone portions, and/or each other, so as to reduce, align, and stabilize one or more bone portions and thereby correct and/or treat a bone fracture. For instance, in certain variations, the bone plate system includes at least a first bone plate, e.g., a diaphyseal bone plate having a flange member extending there from, and a second bone plate, e.g., a peri-articular bone plate, which bone plates may be configured so as to be coupled together and/or to attach to one or more fragmented bone pieces and thereby be used to stabilize, reduce, and/or fix a fractured bone portion for the treatment thereof.

Methods of using such bone plates and bone plate systems for the reduction and/or the restoration and/or treatment of bone fractures, for example, are also provided herein.

BRIEF DESCRIPTION OF THE DRAWINGS

According to common practice, the various features of the drawings may not be presented to-scale. Rather, the dimensions of the various features may be arbitrarily expanded or reduced for clarity. Included in the drawings are the following figures:

FIG. 1 provides a primary bone plate of the present disclosure.

FIG. 2B provides a depiction of the bone plate with flange member as it would be when appropriately positioned so as to reduce, align, and stabilize a bone fracture.

FIG. 3 provides a distal or secondary bone plate that comprises one of at least two bone plates of a bone plate system in accordance with the disclosure.

FIG. 4 provides a bone plate system of the present disclosure.

FIG. 5 provides another variation of a bone plate system of the present disclosure.

Like reference symbols in the various drawings indicate like elements.

DEFINITIONS

Figure 1A:
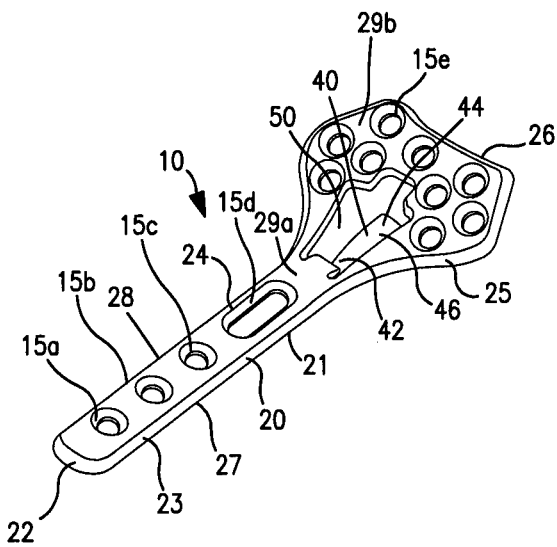
FIG. 1A provides a perspective top view of the primary bone plate.

Before the present subject matter is further described, it is to be understood that this subject matter described herein is not limited to particular embodiments described, as such may of course vary. It is also to be understood that the terminology used here in is for the purpose of describing particular embodiments only, and is not intended to be limiting. Unless defined otherwise, all technical terms used herein have the same meaning as commonly understood by one skilled in the art to which this subject matter belongs.

Where a range of values is provided, it is understood that each intervening value, to the tenth of the unit of the lower limit, unless the context clearly dictates otherwise, between the upper and lower limit of that range, and any other stated or intervening value in that stated range, is encompassed within the subject matter described herein. The upper and lower limits of these smaller ranges may independently be included in the smaller ranges, and are also encompassed within the subject matter described herein, subject to any specifically excluded limit in the stated range. Where the stated range includes one or both of the limits, ranges excluding either or both of those included limits are also included in the subject matter described herein.

It must be noted that as used herein and in the appended claims, the singular forms "a", "and", and "the" include plural referents unless the context clearly dictates otherwise. Thus, for example, reference to a "fastener" includes a plurality of such fasteners, and reference to "the opening" includes reference to one or more openings and equivalents thereof known to those skilled in the art, and so forth.

It is further noted that the claims may be drafted to exclude any optional element. As such, this statement is intended to serve as antecedent basis for use of such exclusive terminology as "solely", "only" and the like, in connection with the recitation of claim elements, or the use of a "negative" limitation. Accordingly, the term "optional" or "optionally present," as in an "optional element," or an "optionally present element," means that the subsequently described element may or may not be present, so that the description includes instances where the element is present and instances where it is not.

As will be apparent to those of skill in the art upon reading this disclosure, each of the individual embodiments described and illustrated herein has discrete components and features which may be readily separated from or combined with the features of any of the other several embodiments without departing from the scope of the subject matter described herein. Any recited method can be carried out in the order of events recited or in any other order which is logically possible.

DETAILED DESCRIPTION

An aspect of the present disclosure includes a bone plate. The bone plate may be used alone or in conjunction with one or more other bone plates to reduce, align, and/or otherwise stabilize a bone fracture. The bone plate may be a primary or secondary bone plate. By "primary" bone plate is meant a bone plate that is configured for being associated with a bone portion, such as a long bone portion, and includes at least a segment that is positioned proximal to a bone fracture. In some embodiments, for instance, where the primary bone plate is to be used by itself to reduce and/or stabilize a fractured bone portion, the bone plate may additionally include a segment that is distal to and spans across a fracture site. In this manner, segments or portions of the bone plate may be associated with both a proximally positioned, non-fractured bone portion and a distally positioned, fractured bone portion, where the segments of the bone plate span across a fracture site.

In some embodiments, the primary bone plate is configured for being associated with another bone plate, such as a secondary bone plate. Accordingly, the primary bone plate may be the bone plate that is configured for being associated with a non-fractured, proximally positioned bone portion, and the secondary bone plate may be a bone plate that is configured for being associated with a fractured, distally positioned bone portion. In such an instance, the primary and secondary bone plates may be configured for being associated with separate bone portions, such as bone portions that are opposite a fracture site, and are configured for being coupled with one another, so as to reduce, align, and/or otherwise stabilize a bone fracture.

A bone plate of the disclosure may have any suitable shape and have any suitable size, so long as the bone plate includes an extended body that is capable of being attached to a bone portion. In certain embodiments, a bone plate of the disclosure includes at least one flange member extending from an extended body of the bone plate. The bone plate including a flange member may be a primary bone plate or a secondary bone plate. The flange member may be an element that is configured to assist in the stabilization and/or reduction of a fracture of a bone portion so as to treat the bone fracture. For instance, a bone plate of the disclosure may be an elongate plate member that includes a proximal portion with a proximal end, a distal portion with a distal end, and an intercalating portion disposed between the proximal and distal portions, which may be referenced herein as plate segment, where at least one of the proximal, intercalating, and distal portions includes at least one flange member extending there from Specifically, the first and second ends of the bone plate are separated from one another by a separation that defines a length of the subject bone plate. In certain embodiments, and dependent on the context, the proximal portion of the bone plate refers to a region of the bone plate that is positioned toward or closer to the core of the subject's body upon which the bone plate is to be applied. A distal portion of the bone plate refers to a region of the bone plate that is positioned away from the core of the subject's body upon which the bone plate is to be applied.

A bone plate of the invention may additionally include a top and a bottom surface as well as a first and a second side. The top and bottom surface are separated from one another by a distance, which distance defines a thickness. The first and second sides are also separated from one another, which separation defines a width. The bottom surface may be configured for contacting a bone surface, and may be referenced herein as a bone contacting surface. The top surface is opposite the bone contacting surface.

The bone plate may have a length that ranges from about 3 mm or less to about 70 mm or more, such as about 5 mm or 8 mm to about 30 mm, for instance, between about 10 mm or 12 mm to about 25 mm, such as between about 15 mm to about 20 mm. The bone plate may have a thickness that ranges from about 0.01 mm or less to about 3 mm or more, for instance, between about 0.1 mm to about 2.5 mm, such as between about 0.5 mm or about 1 mm to about 1.5 mm or about 2 mm. A bone plate of the subject disclosure may have a width that ranges from about 3 mm or less to about 30 mm or more, for instance, between about 4 mm to about 25 mm, such as between about 5 mm or about 8 mm to about 15 mm or about 18 mm, for instance, about 10 mm to about 12 mm.

The length of the bone plate may be fixed or it may be variable. For instance, the bone plate may include an intercalating portion wherein the length of the intercalating portion may be variable. For instance, the intercalating portion may be fabricated from a material and in such a manner that it resists deformation, or it may be fabricated from a material and in such a manner that it is capable of being bent or shaped before use. Accordingly, the length and/or shape of the intercalating portion may be fixed or adjustable. For example, the intercalating portion may be adjustable, and therefore may include a groove and or slot configuration whereby the proximal and distal portions of the bone plate may be adjusted longitudinally with respect to one another, such as by sliding of one portion in relation to the other. Thus, the intercalating portion may be configured for sliding in the proximal-distal direction so as to decrease and/or increase in length. An opening may also be included in the intercalating portion, such that a fastener may be received there through for locking the adjustable length of the intercalating portion and/or the bone plate as whole in a fixed configuration.

In certain embodiments, the bone plate includes a portion that contains at least one flange member. For instance, a proximal, intercalating, or distal portion of the bone plate may include the flange member. In certain embodiments, a distal portion of the bone plate includes the flange member. The flange member may have any suitable configuration so long as at least a portion of the flange member is configured for contacting or otherwise engaging a bone portion, such as a fractured and/or fragmented bone portion to which the bone plate is to be associated.

For example, the flange member may be configured as an extended body that is positioned at least partially below the bottom surface of the elongated body. For instance, the flange member may include a stabilization member, which member may include a surface, such as a bone engaging surface that is displaced from a bottom surface of the elongated body of the bone plate and extends away there from. The flange member, therefore, may include one or more portions, such as a portion that extends away from the elongated body, e.g., a portion that transects and extends downwards away from the elongated body, and a portion (e.g., a stabilizing portion) that is displaced from the elongated body and extends in a direction that is parallel or anti-parallel to the elongated body.

Accordingly, the extended body of the flange member may include a connector portion that extends away from the bottom surface of the elongated body, and a bone engaging portion that is displaced from the elongated body, e.g., via the connector, and extends in a direction that is parallel or anti-parallel to the elongate body.

The flange member may be integral and contiguous with the elongated body of the bone plate or may be a separate piece attached to the elongate body. Accordingly, the flange member may be configured such that it is formed from a surface of the elongated body, is contiguous therewith but extends away there from, or the flange member may be a separate element that is associated with or otherwise attached to the bottom surface of the elongated body of the bone plate.

For instance, in certain embodiments, the flange member is fabricated from the material of which the elongated body of the bone plate is made, such that the elongated body and the flange member form a singular whole. Specifically, the flange member may be formed from separating the connector portion and the extended body portion from a surface of the elongated body of the bone plate.

For instance, the flange member may be a cut out portion of the elongated body of the bone plate. In some embodiments, the bottom surface of the elongated body may include a primary bone engaging surface, configured for engaging a bone portion, such as an extramedullary bone portion, and the flange member may be a portion of the bottom surface that is cut out from the elongated body and displaced there from so as to form the connector and extended body, such that the flange member, or at least a surface thereof, such as a secondary bone engaging surface, may be positioned within the footprint of the primary bone engaging surface and may be configured for engaging an intramedullary bone portion. Specifically, due to the configuration of cut out portion and the way it was formed, the cut out may form a cut out aperture in the elongated body of the bone plate, wherein the dimensions of the cut out may fit within the dimensions of the cut out aperture.

Accordingly, the bone plate may include an elongated body that includes a bottom surface, which bottom surface includes a primary bone engaging portion, and a flange member that includes an extended body, which extended body includes a top and a bottom surface, which top surface includes a secondary bone engaging portion. In certain embodiments, the primary bone engaging surface is configured for engaging a bone portion, such as an extramedullary bone portion, and the secondary bone engaging surface is also configured for engaging bone portion, such as an intramedullary bone portion. In some embodiments, the extramedullary bone portion and the intramedullary bone portion comprise the same bone portion. In some embodiments, the top or secondary bone engaging surface of the extended body of the flange member is coextensive with the bottom surface of the elongated body. For instance, the dimensions of the extended body of the flange member may be such that the extended body does not extend beyond the bounds of the length or width dimensions of the elongated body, e.g., the length and width of the extended body of the flange member is less than the length and/width of the elongated body. Although, in some embodiments, the length and/or width of the extended body of the flange member may be greater than the length and/width of the elongated body.

The connector portion of the extended body of the flange member, if included, may have any suitable configuration, so long as it is capable of connecting the flange member to a surface, such as a bottom surface, of the elongated body of the bone plate, and/or displacing the extended body, e.g., the bone engaging portion, of the flange member a distance from the surface of the bone plate. The connector may be contiguous with one or more of the elongated body of the bone plate and/or the extended body of the flange member, or it may be a separate element attached to one or more of the elongated and extended bodies. Accordingly, the connector portion is a body that has a plurality of surfaces and includes a length, width, and height dimension.

Hence, the connector includes a length that ranges from about 1 mm or less to about 10 mm or more, for instance, between about 2 mm to about 8 mm, such as between about 4 mm to about 6 mm. Further, the connector may include a width that ranges from about 2 mm or less to about 20 mm or more, for instance, between about 5 mm to about 15 mm, such as between about 8 mm to about 10 mm. Additionally, the connector may include a height that ranges from about 0.2 mm or less to about 5 mm or more, for instance, between about 0.5 mm to about 3 mm, such as between about 1 mm to about 2 mm.

The connector may have any suitable shape and may be round, triangular, pyramidal, square, rectangular, and the like.

In certain embodiments, the connector portion is an extended post like element that connects a top surface of the bone engaging portion of the flange member to a bottom surface of the elongated body of the bone plate. Accordingly, at least a portion of the bone engaging portion of the flange member will be displaced from the bottom surface of the elongated body by a distance that is equal to the height of the post like element. This distance, however, may vary dependent upon the configuration of the bone engaging portion and the nature of its association with the connector portion.

The bone engaging portion of the extended body of the flange member may be of any suitable configuration, so long as it includes a plurality of surfaces, such as a top and a bottom surface, one or more of which surfaces are adapted for engaging a bone portion, such as a fractured bone portion, so as to assist in the stabilization and reduction of the fractured bone. The bone engaging member may be directly associated with a bottom surface of the elongated body of the bone plate, or the bone engaging member may be indirectly associated with a bottom surface of the elongated body of the bone plate, e.g., via an intervening connector element.

For instance, the bone engaging portion includes an extended body. The extended body may be of any suitable shape including circular, oval, elliptical, triangular, square, rectangular, hexagonal, and the like. In some embodiments, the flange member includes a connector and an extended body that are configured in the shape of an "L," with the connector comprising the short portion of the "L" and the extended body comprising the long portion of the "L." The extended body includes a length, width, and height dimension. Such as a length that ranges from about 1 mm to about 30 mm or more, for instance, between about 5 mm to about 25 mm, such as between about 10 mm to about 20 mm, including about 15 mm. Further, the extended body may include a width that ranges from about 2 mm or less to about 20 mm or more, for instance, between about 5 mm to about 15 mm, such as between about 8 mm to about 10 mm. Additionally, the extended body may include a height that ranges from about 0.2 mm or less to about 5 mm or more, for instance, between about 0.5 mm to about 3 mm, such as between about 1 mm to about 2 mm. In certain variations, the bone engaging portion is an extended body that includes a proximal portion, intercalating portion, and a distal portion. Additionally, the bone engaging portion includes a plurality of surfaces, which surfaces correspond to the proximal, intercalating, and distal portions. In one embodiment, a top surface of the bone engaging portion of the flange member includes a secondary bone engaging surface. Dependent on its context, the proximal portion of the bone engaging portion of the flange member is typically defined herein as the portion closer to the proximal portion of the elongated body of the bone plate. For instance, the portion that contacts the elongated body of the bone plate or the connector, which connector contacts the elongated body of the bone plate. The distal portion is typically defined herein as the portion that is closer to the distal portion of the elongated body of the bone plate, for instance, the portion that is further away from the connector, which connector contacts the elongated body of the bone plate.

The plurality of surfaces of the bone engaging portion of the extended body may include a top and a bottom surface. For instance, the bone engaging portion of the flange member may include a top and bottom surface one or both of which are planar or non-planar. For example, the bone engaging portion may include a top and/or a bottom surface that corresponds to each of a proximal, intercalating, and distal portion, wherein the proximal, intercalating, and distal portions are of equivalent dimensions and aligned such that the top and/or bottom surface are substantially planar. Alternatively, one or more of the proximal, intercalating, and distal portion may be configured such that it is angled with respect to one or more of the other portions, such that the top and/or bottom surface may include an angle, arc, or curve.

Accordingly, the top or bottom surface of the bone engaging portion of the flange member may be linear or otherwise planar, or the top or bottom surface may be non-linear or otherwise non-planar, for instance, it may be angled, arced, or curved. For instance, one or more of the proximal, intercalating, and distal portions may be angled with respect to the other such that the top and/or bottom surface may include an internal angled portion, wherein the angle may range from about 1° to about 90°, such as from about 5° to about 45°, for instance from about 7.5° to about 30°, including from about 10° to about 20°, such about as 15°. Further, the top and/or bottom surface may include an internal curved or arced portion, wherein the arc includes a radius of curvature that ranges from about 1 mm to about 50 mm, for instance, from about 5 mm to about 30 mm, including from about 10 mm to about 20 mm, such about as 15 mm.

In some variations, the bone engaging portion of the flange member may directly contact and/or be directly associated with a surface, such as a bottom surface, of the bone plate. For instance, the flange member may simply be a cut-out section of the bone plate, which cut-out section is integral with the elongated body of the bone plate and extends downwards away from a bottom surface of the elongated body. For example, where a bottom surface of the elongated body of the bone plate corresponds to a first plane, the flange member may simply be comprised of a planar bone engaging portion that extends away from the bottom surface of the elongated body such that a secondary plane corresponding to the top or bottom surface of bone engaging portion transects the primary plane of the bottom surface of the elongated body of the bone plate. In such an embodiment, a connector portion may not be included. Accordingly, the flange member may be angled with respect to a bottom surface of the elongated body of the bone plate, and/or a plane defined thereby, which angle may range from about 0° to about 90°, such as about 5° to about 60°, for instance, about 10° to about 45°, including about 20° to about 30°.

Alternatively, the bone engaging portion of the flange member may indirectly contact and/or be indirectly associated with a bottom surface of the bone plate. For instance, the flange member may include a connector portion. A connector portion may be included, for example, where it is desired to distance a top and/or bottom surface of the bone engaging portion of the flange member away from the bottom surface of the elongated body of the bone plate. Accordingly, in this instance, the flange member may still be a cut-out section that is integral with the elongated body of the bone plate, however, a connector portion, where included, separates the bone contacting portion of the flange member from the bottom surface of the elongated body of the bone plate. Hence, in accordance with this variation, the flange member may be a cut out section of the elongated body of the bone plate that includes two portions, one portion that extends downwards away from the bottom surface of the elongated body of the bone plate, and/or a plane defined thereby, and one portion that extends axially away from the connector portion.

For example, the bone plate may include an elongate body having a bottom surface, which bottom surface corresponds to a first plane. The bone plate may further include a flange member that in turn includes two portions: a connector portion and a bone engaging portion. The bone engaging portion may include a top and bottom surface, which top or bottom surface correspond to a second plane. The connector portion may also include a surface that corresponds to a third plane. Accordingly, the bone plate may include a flange member, which flange member may include a connector that is associated with the bottom surface of the elongate body of the bone plate and extends downwards away from the bottom surface such that the $1^{st}$ and 3rd planes transect one other. Further, the flange member may include a bone engaging portion that is associated with the connector in such a manner that the $2^{nd}$ and $3^{rd}$ planes transect one another. It is to be noted that dependent on the configuration of the connector portion and the nature of the association between the connector portion and the bone engaging portion, the $1^{st}$ and third planes may either be substantially parallel to one another, or transect one another and may be displaced from one another by a distance determined by one or more of the dimensions of the connector.

Hence, one or more of the $1^{st}$, $2^{nd}$ and/or 3rd planes, may be parallel or angled with respect to each other. Thus, the surfaces corresponding to the bottom surface of the elongated body of the bone plate as well as the a surface of the connector and a surface of the bone engaging portion of the flange member may be angled with respect to one another, such that the surfaces pertaining thereto transect one another. The angle may be any suitable angle, for instance, an acute, perpendicular, or obtuse angle, and thus may range, for instance, from about 1° to about 179°, such as from about 5° to about 160°, for instance from about 7.5° to about 120°, including from about 10° to about 100°, such about as 15°.

The flange member may be connected to a surface of the elongated body at a proximal, intercalating, or distal portion. For instance, the distal portion of the elongated body may include a top and a bottom surface, to which bottom surface the flange member is connected. The bottom surface may include a primary bone engaging portion and may include the flange member portion. The flange member may include a connector portion and/or an extended body that includes a top surface, which top surface includes a secondary bone engaging portion.

The flange member may include a portion that is extramedullary and a portion that is intramedullary. For instance, the connector portion may be an extramedullary portion, and the extended body, e.g., the secondary bone engaging surface thereof, may be an intramedullary portion. In certain instances, both portions may be intramedullary. Accordingly, the bone plate may be configured such that the primary bone engaging surface of the bottom surface engages a bone portion, such as an extramedullary bone portion, and the secondary bone engaging surface of the flange member engages a bone portion, such as an intramedullary bone portion. In some embodiments, the engaged bone portion comprises the same bone portion, for instance, where a portion of the bottom surface of the elongated body engages an outer portion of the bone, and the top surface of the flange member engages the inner portion of the same bone, such that the bone is sandwiched between the two surfaces.

In certain variations the extended body of the flange member includes an opening, for instance an opening through which a fastener may be inserted. For example, in certain embodiments, the bone plate and flange member include openings that are configured such that a fastener may be inserted through an opening in a surface of the elongated body of the bone plate and extend there through and into a corresponding opening in the flange member. In such an embodiment, a locking element may be included so as to lock the inserted fastener in place.

The flange member may be fabricated from a single piece of material, such as from the same material from which the elongate body portion of the bone plate is fabricated, and thus, may be an integral part of the bone plate, e.g., and coextensive with the elongated body; or it may be fabricated from one or more separate pieces that are subsequently attached to the elongate body of the bone plate. Accordingly, a bone plate of the present disclosure, for instance, a primary or secondary bone plate with a flange member, may be fabricated from any suitable material and in any suitable manner.

Specifically, a subject bone plate of the disclosure, or a portion thereof, may be fabricated from any suitable biocompatible material so long as the bone plate(s) is of sturdy yet malleable construction. For instance, in certain embodiments, the bone plate may be fabricated from a suitable metal material containing a metal such as stainless steel, titanium, cobalt chromium, and/or an alloy thereof. Further, suitable materials may be a bioabsorbable material such as polygalactic acid (PGA), polylactic acid (PLA), copolymers thereof, and the like. Other suitable materials include plastic, ceramics, and the like. In general, the bone plate may be fabricated from a suitable material so as to resist deformation and to be stiffer and stronger than the section of bone spanned by the extender plate, yet flexible enough not to significantly strain the bone. In certain embodiments, the bone plate and/or flange member may be fabricated in accordance with methods including stamping, machining, casting, laser cutting, molding, and the like.

In certain embodiments, the bone plate or a portion thereof may be fabricated from a material that may be bent or formed intraoperatively to accommodate the shape of the bone. For instance, the type and strength characteristics of the material used to form the bone plate, or a portion thereof, may be selected such that the material and the portion it comprises is such that it may be malleable and deformed as desired and yet keep the shape of the deformation.

Dependent on the dimensions and shape of its configuration and the use to which it is to be put, the bone plate with flange member may be adapted so as to be associated with any suitable bone portion. For instance, in some embodiments, the bone plate is a primary bone plate that is configured for being associated with, e.g., attached to, a shaft portion of a long bone. For instance, in certain embodiments, the primary bone plate is configured for being attached to a diaphyseal portion of a bone, and therefore, the primary bone plate may be referenced herein as a diaphyseal bone plate.

Accordingly, a primary bone plate, e.g., a diaphyseal bone plate, of the disclosure may be configured so as to be complimentary to a bone morphology, such as the long bone morphology of a diaphyseal bone. In certain embodiments, the primary bone plate has a configuration that is complimentary to a planar portion of a bone portion, e.g., a diaphyseal bone portion, and in certain embodiments, the primary bone plate has a configuration that is complimentary to a non-planar portion of a bone portion. For instance, in certain variations, a bone plate of the disclosure may have a configuration that corresponds to a volar or dorsal distal radius surface.

Hence, the primary bone plate may be substantially planar, for instance, where the proximal and distal ends of the bone plate define a primary plane. For instance, in certain embodiments, at least one of the primary bone plate bone contacting surface and the primary bone plate top surface substantially corresponds to a primary plane, wherein the primary plane is substantially linear. However, in certain embodiments, at least one of the primary bone plate bone contacting surface and the primary bone plate top surface corresponds to a primary plane, wherein the primary plane is non-linear, or arced.

For example, the primary bone plate may be non-planar and may have a configuration that is adapted to conform to a specific non-planar bone morphology, such as a configuration that is adapted to specifically and snugly fit the bone morphology to which the bone plate is to be associated and/or attached. Hence, in certain embodiments, the primary bone plate includes an internal angled and/or arced portion between the proximal and distal ends thereof and is therefore angled and/or arced in correspondence to a bone surface to which the plate is to be associated.

For instance, in certain embodiments, the bone contacting surface between the proximal and distal ends of the primary bone plate may include an internal angled portion, wherein the angle may range from about 1° to about 90°, such as from about 5° to about 45°, for instance from about 7.5° to about 30°, including from about 10° to about 20°, such about as 15°. The bone contacting surface between the proximal and distal ends of the primary bone plate may include an internal arced portion, wherein the arc includes a radius of curvature that ranges from about 1 mm to about 50 mm, for instance, from about 5 mm to about 30 mm, including from about 10 mm to about 20 mm, such about as 15 mm.

Further, in certain embodiments, the primary bone plate includes a curved portion between the first and second sides thereof and is therefore curved relative to a central, longitudinal axis defined by the proximal and distal ends of the primary bone plate. For instance, in certain embodiments, the primary bone plate may include an internal concave portion between the first and second sides of the bone plate. The concaved portion may run along a partial or entire length of the primary bone plate, wherein the curvature comprises a degree of curvature, e.g., a concavity that ranges from about 5 mm to about 20 mm, such as about 7 mm to about 18 mm, including about 10 mm to about 15 mm.

In certain embodiments, the bone plate includes a groove. For example, in certain embodiments, the proximal portion of the primary bone plate, e.g., the portion adapted to be associated with a first bone portion, may include a concave configuration or groove, e.g., a groove adapted to fit around a convex bone portion, while the distal portion is substantially planar. In certain embodiments, the distal portion of the primary bone plate may include a concave configuration or groove while the proximal portion is substantially planar.

In certain embodiments, the distal portion of the primary bone plate may be planar, and a top or bottom surface of the primary bone plate may include a slot portion that is configured for receiving an insertion member, e.g., a tab insertion portion, of a secondary bone plate. Accordingly, although in some embodiments, the primary bone plate is configured for engaging and/or being affixed or otherwise associated with a bone portion without being associated with or coupled to a secondary bone plate; in other embodiments, the primary bone plate is configured for being affixed or otherwise associated with a bone portion and is adapted for engaging or being associated with an additional, e.g., secondary bone plate.

For instance, the proximal portion of the primary bone plate may be configured for engaging or otherwise being associated with a portion of bone, e.g., a first bone portion, and the distal portion may be configured for being associated with an additional bone plate and/or another portion of bone, e.g., a second bone portion. Specifically, in certain embodiments, the distal portion of the primary bone plate may include a plate engagement element, such as a peri-articular bone plate engagement element, e.g., where the secondary bone plate is a peri-articular bone plate.

Accordingly, another aspect of the present disclosure includes a bone plate system. The bone plate system may include at least a first bone plate, such as a bone and a second bone plate, which bone plates may be affixed to one or more bone portions and/or each other, so as to align and stabilize the bone and thereby correct and/or treat a bone fracture. In some variations, at least one of the primary and secondary bone plates includes a flange member, as described above. Thus, in certain variations, the bone plate system disclosed herein may include at least a primary bone plate and a second bone plate, at least one of which included a flange member, and which bone plates may be configured so as to be coupled together and/or to attach to one or more fragmented bone portions and thereby be used to reduce and/or fix a fractured bone portion for the treatment thereof.

Hence, where included, a bone plate engagement element of the primary or secondary bone plate may have any suitable configuration so long as it is capable of facilitating an association and/or coupling of a one bone plate with an additional bone plate. For instance, the engagement element of a primary bone plate may be a configuration that is adapted to allow the primary bone plate to be associated with a secondary bone plate. Hence, an engagement element of a bone plate of the invention may include a recess, groove or slot-like configuration positioned at a distal portion of the bone plate, which is adapted to receive a corresponding engagement portion, e.g., a tab portion, of another bone plate and thereby be mated therewith.

For example, where a primary bone plate includes an engagement element configured as a tab receiving portion, a secondary bone plate may include an engagement element (e.g., a primary bone plate engagement element) configured as an extended male insertion portion (e.g., a tab insertion portion). Accordingly, a bone plate, such as a primary bone plate, may include a recessed engagement portion (e.g., a secondary bone plate engagement element) that is configured as a grooved, hooded, and/or cut-out female tab receiving portion that is adapted to receive the insertion portion of another, e.g., secondary, bone plate. The tabbed receiving portion may be formed on a top or a bottom surface of the bone plate.

Hence, in one embodiment, the engagement element of the primary bone plate may be configured as a grooved portion within which is fitted the tab insertion portion of the secondary bone plate. Accordingly, the primary bone plate engagement element may include one or both of a recessed portion and a groove-like configuration in to which the insertion portion slides. In certain embodiments, the engagement element is hooded, e.g., the distal end of the primary bone plated includes a slot or an orifice into which the tab portion of an additional plate is inserted. In certain embodiments, the recessed portion forms a quadrilateral.

Accordingly, in certain embodiments, the engagement element of a bone plate of the disclosure, e.g., a primary bone plate, is configured as a receptacle or tab receiving portion, wherein the receptacle portion has a first width that ranges from about 2 mm to about 20 mm, for instance, between about 5 mm to about 15 mm, such as between about 7 mm and about 10 mm. In certain embodiments, the receptacle portion has a second width that ranges from about 1 mm to about 18 mm, for instance, between about 3 mm to about 14 mm, such as between about 5 mm and about 7 mm or about 8 mm or about 10 mm. In certain embodiments, the first and second widths are distanced from one another such that the receptacle or tab receiving portion tapers along its length. In certain embodiments, the engagement element may have a length that ranges from about 5 mm to about 30 mm, for instance, between about 7.5 mm to about 25 mm, such as between about 10 mm to about 15 mm or about 20 mm. In certain embodiments, the engagement member may have a thickness that ranges from about 0.1 mm to about 3 mm, for instance, between about 0.25 mm to about 2 mm, such as between about 0.5 mm or 1 mm to about 1.5 mm.

The distal portion of the primary bone plate may itself be angled with respect to the proximal portion and/or a proximal end of the primary bone plate. For instance, a plane defined by a top surface of the distal portion of a primary bone plate elongated body may be angled with respect to the a plane defined by a top surface of the proximal portion of the primary bone plate elongated body such that an engagement element positioned at the distal portion of the primary bone plate is angled with respect to the proximal portion of the primary bone plate. In certain embodiments, the angle between the planes defined by the two surfaces may range from about 1° to about 90°, such as from about 5° to about 45°, for instance from about 7.5° to about 30°, including from about 10° to about 20°, such about as 15°. In certain embodiments, the engagement element positioned at the distal portion of the primary bone plate is not angled but rather is planar with respect to the proximal end of the primary bone plate.

As indicated above, in one aspect the present disclosure is directed to a bone plate system that includes a second bone plate (sometimes referred to herein as a secondary bone plate. A secondary bone plate of the subject bone plate system may have any suitable shape and have any suitable size so long as the secondary bone plate is capable of being coupled to a primary bone plate and/or associated with a bone portion, e.g., a second and/or third bone portion, so as to assist in the reduction and/or stabilization of one or more bone portions and thereby treat a bone fracture.

The secondary bone plate may be an extended bone plate member that includes a proximal portion which is configured for being coupled to a primary bone plate, such as a primary bone plate and/or associated with or other wise attached to a portion of bone, e.g., a second bone portion, and additionally includes a distal portion that is configured for being contacted and/or attached to another bone portion, e.g., a third bone portion. The secondary bone plate may further include an intercalating portion, as described above, interposed between the proximal and distal portions. Additionally, the secondary bone plate may include a bottom surface that is configured for contacting a bone surface and therefore may be referenced as a bone contacting surface. Likewise, in certain embodiments, the secondary bone plate includes a top surface that is opposite the bone contacting surface. In certain embodiments, the secondary bone plate includes a flange member, such as a flange member as described above. Further, the secondary bone plate includes at least a first side and a second side which sides are separated from each other by a distance, which distance defines a width.

In certain embodiments, the secondary bone plate may have a length that ranges from about 5 mm or less to about 50 mm or more, such as about 8 mm to about 30 mm, for instance, between about 10 mm to about 25 mm, such as between about 12 mm to about 15 mm. In certain embodiments, the secondary bone plate may have a thickness that may range from about 0.01 mm or less to about 4 mm or more, for instance, between about 0.1 mm to about 3 mm, such as between about 0.5 mm or about 1 mm to about 2 or about 2.5 mm. In certain embodiments, a suitable secondary bone plate of the subject disclosure may have a width that ranges from about 2 mm or less to about 50 mm or more, for instance, between about 4 mm to about 40 mm, such as between about 5 or about 8 mm to about 25 mm or about 30 mm, for instance, about 10 mm to about 12 mm.

The proximal portion of secondary bone plate may include a primary bone plate engagement element. A primary bone plate engagement element of the secondary bone plate may have any suitable configuration so long as it is capable of facilitating an association and/or coupling of the secondary bone plate with a primary bone plate. For instance, as described above, the engagement element of the secondary bone plate may include a configuration that is adapted to allow the secondary bone plate to be associated with a first bone plate, e.g., a primary bone plate.

Hence, the secondary bone plate engagement element may include an extended portion, such as a tab insertion portion, that is configured for being inserted or otherwise associated with a groove, hooded, and/or slot-like configuration of a primary bone plate, wherein the engagement portion is positioned at a proximal portion of the secondary bone plate and is adapted to be coupled to a corresponding engagement portion, such as a tab receiving portion, of a primary bone plate and thereby be mated therewith. For example, where a primary bone plate includes an engagement element (e.g., a primary bone plate engagement element) configured as a female receiving portion (e.g., an insertion tab receiving portion), the secondary bone plate may include an extended engagement portion (e.g., a secondary bone plate engagement element) that is configured as an insertion member or tab that is adapted to be received within the receiving portion of the primary bone plate.

Accordingly, in certain variations, the engagement element of the secondary bone plate is configured as a tab insertion portion, wherein the tab insertion portion has a first width that ranges from about 1 mm or slightly less than 2 mm to about 18 mm or slightly less than 20 mm, for instance, between about 3 mm or slightly less than 5 mm, to about 14 mm or slightly less than 15 mm, such as between about slightly less than 7 mm to about slightly less than 10 mm. In certain variations, the tab insertion portion has a second width that ranges from about 1 mm to about slightly less than 18 mm, for instance, between about 3 mm or slightly less than 4 mm to about slightly less than 14 mm, such as between about 5 mm and about slightly less than about 7 mm or about 8 mm or about slightly less than 10 mm. In certain embodiments, the first and second widths are distanced from one another such that the tab insertion portion tapers along its length. In certain variations, the tab insertion portion may have a length that ranges from about 3 mm to about slightly less than 30 mm, for instance, between about 5 mm or slightly less than 6 mm to about slightly less than 25 mm, such as between about slightly less than 10 mm to about slightly less than about 15 mm or about 20 mm. In certain variations, the engagement element may have a thickness that ranges from about 0.1 mm to about 3 mm, for instance, between about 0.25 mm to about 2 mm, such as between about 0.5 mm or 1 mm to about 1.5 mm.

It is to be noted that with respect to the above descriptions, the primary bone plate is described as including a female receiving engagement element, and the secondary bone plate is described as including a male insertion engagement element. Nevertheless, in certain embodiments, the primary bone plate includes a male insertion or tab-like engagement element, as that element is described above with respect to the secondary bone plate, and the secondary bone plate includes a female or tab receiving engagement element, as that element is described above with respect to the primary bone plate.

In certain variations, the engagement element positioned at the proximal portion of the secondary bone plate, and in some cases the proximal portion itself, is angled with respect to a distal portion and/or distal end of the secondary bone plate. For instance, a plane defined by a top surface of the proximal portion of the secondary bone plate body may be angled with respect to a plane defined by a top surface of the distal portion of the secondary bone plate body such that an engagement element positioned at the proximal portion of the secondary bone plate is angled with respect to the distal portion of the secondary bone plate.

Accordingly, in certain variations, the proximal portion containing the engagement element of the secondary bone plate may be angled with respect to the distal portion or vice-versa. For instance, in certain variations, there is an angle between the engagement element portion of the proximal portion of the secondary bone plate and the rest of the plate. In certain variations, the angle between the engagement element of the secondary bone plate and the rest of the plate may range from about 1° to about 90°, such as from about 5° to about 45°, for instance from about 7.5° to about 30°, including from about 10° to about 20°, such about as 15°. However, in certain variations, the engagement element positioned at the proximal portion of the secondary bone plate is not angled but rather is planar with respect to the distal end of the secondary bone plate.

In some variations, the secondary bone plate is configured for being associated with, e.g., contacted with and/or attached to a bone portion, such as an articulated portion of a bone, for instance, as a metaphyseal or epiphyseal bone portion. For example, in certain embodiments, the secondary bone plate may be configured for being attached to a peri-articular or juxtaarticular portion of a bone, and therefore, the secondary bone plate may be referenced as a peri-articular or juxtaarticlar bone plate. Hence, the secondary bone plate, e.g., a peri-articular or juxtaarticular bone plate, may be configured so as to be complimentary to a bone morphology, such as the articulated bone morphology of a metaphysis or epiphysis bone portion. Accordingly, the secondary bone plate may have a configuration that is complimentary to a non-planar portion of an articulated bone portion.

For instance, the secondary bone plate may have a configuration that is adapted to conform to a specific bone morphology, such as a configuration that is adapted to specifically and snugly fit the bone morphology to which the secondary bone plate is to be contacted, associated, and/or attached. Thus, in certain embodiments, the secondary bone plate is non-planar. Consequently, there may be an angle between the proximal and distal portions of the secondary bone plate.

For example, in certain variations, a bone contacting surface of a proximal portion of a secondary bone plate may constitute a first or proximal plane of the secondary bone plate, and a bone contacting surface of a distal portion of a secondary bone plate may constitute a second or distal plane of the secondary bone plate, wherein the proximal and distal planes of the secondary bone plate are transverse to one another. Hence, the bone contacting surface between the proximal and distal portions and/or ends thereof of the secondary bone plate may include an internal angled portion. Accordingly, the angle between the planes defined by the proximal and distal bone contacting surfaces of the secondary bone plate may range from about 1° to about 90°, such as from about 5° to about 45°, for instance from about 7.5° to about 30°, including from about 10° to about 20°, such about as 15°. Additionally, although there may be an angle between the proximal and distal portions of the secondary bone plate, in certain variations, the proximal portion of the secondary bone plate is not angled with respect to a primary plane as defined by the primary bone plate. For instance, in certain variations, the proximal portion of the secondary bone plate is substantially coplanar with a primary plane of the primary bone plate.

Thus, in certain variations, the secondary bone plate includes an internal angled, curved, and/or arced portion between the proximal and distal ends thereof and is therefore angled, curved and/or arced in correspondence to a bone surface to which the plate is to be associated so as to model the morphology of the bone surface. Hence, the bone contacting surface between the proximal and distal ends of the secondary bone plate may include an internal curved portion, wherein the curve includes a degree of curvature that ranges from about 10 mm to about 50 mm, for instance, between about 15 mm to about 35 mm, such as between about 18 mm or about 20 mm to about 25 or about 30 mm.

Further still, in certain exemplary variations, the bone contacting surface between the proximal and distal ends of the secondary bone plate may include an internal arced portion, wherein the arc includes a radius of curvature that may be constant, increasing, or decreasing, depending in part on the length of the intercalating portion of the secondary bone plate. Accordingly, in certain variations, a bone contacting surface of the secondary bone plate includes an arc that has a decreasing radius of curvature that ranges from about 10 mm to about 50 mm, for instance, between about 15 mm to about 35 mm, such as between about 18 mm or about 20 mm to about 25 or about 30 mm. In certain embodiments, the secondary bone plate includes a curved and/or twisted portion whereby the twisted portion allows the secondary bone plate to extend outward and away from a primary bone plate so as to contact a bone surface that is positioned distally and out of plane with a bone contacting surface and/or a primary plane of the primary bone plate.

In certain variations, the secondary bone plate includes a curved or concave portion between the first and second sides thereof and is therefore curved relative to a central, longitudinal axis defined by the proximal and distal ends of the secondary bone plate. For instance, in certain variations, the secondary bone plate may include an internal concave portion between the first and second sides of the bone plate. The concaved portion may run along a partial or entire length of the secondary bone plate, wherein the curvature comprises a degree of curvature, e.g., a concavity, that ranges from about 5 mm to about 30 mm, for instance, between about 8 mm to about 30 mm, such as between about 10 mm or about 12 mm to about 20 mm or about 25 mm. In certain embodiments, the proximal portion includes a concaved portion, while the distal portion does not, e.g., a portion between the first and second sides of the secondary bone plate along the distal portion of the secondary bone plate are substantially flat or planar, and in certain embodiments, the distal portion includes a concaved portion, while the proximal portion does not.

In certain variations, the secondary bone plate of the bone plate system includes a distal portion that is angled, curved, or arced, as described above, relative to a proximal portion, wherein the proximal portion of the secondary bone plate is relatively planar in relation to a primary plane defined by a top or bone contacting surface of the primary bone plate. In other variations, the proximal portion is angled, curved, or arced with respect to a primary plane defined by a top or bone contacting surface of the primary bone plate, but is in plane internally with respect to the distal portion of the secondary bone plate, that is the distal and proximal ends of the secondary bone plate may be in plane with one another (e.g., thus forming a secondary plane there between), which plane may transect or otherwise be out of plane from the primary plane of the primary bone plate. Accordingly, a portion or the entire secondary bone plate may be angled or curved with relationship to the primary bone plate.

In view of the above, the secondary bone plate may be angled in relationship to the primary bone plate in numerous ways such that the secondary bone plate includes a bone contacting surface that corresponds to one or more planes or an arc that are provided at an angle or substantially perpendicular to a primary plane defined by a primary bone plate. Accordingly, in certain variations, the secondary bone plate is angled with respect to a primary plane defined by the primary bone plate, wherein the angle may range from about 1° to about 90°, such as from about 5° to about 45°, for instance from about 7.5° to about 30°, including from about 10° to about 20°, such about as 15°.

In certain variations, a bone plate of the disclosure may include a plurality of segments or sections. For instance, in certain variations, the bone plate may include a first section, wherein the first section includes a bone plate engagement element, and a second section, wherein the second section includes a configuration adapted for contacting a bone surface. In certain variations, the second section is transverse to the second section.

For example, in certain variations, the bone plate may be configured so as to have a substantially "T" shape. Specifically, the first section may include a proximal portion with a proximal end, a distal portion with a distal end, and an intercalating portion; and the second section may be transverse to the first section and may include a proximal portion with a proximal end, a distal portion with a distal end, and an intercalating portion, wherein the intercalating portion, or another portion, of the second or transverse section is bisected by the distal portion of the first section, such that the secondary bone plate forms a "T" shape.

In certain variations, a first section of the bone plate is angled in relation to the second section. For instance, a top or bottom surface of the proximal portion of the first section may define a first plane, and a top or bottom surface of the distal portion of the first section and/or a top or bottom surface of the second section may define a second plane, wherein the first and second planes transect one another, such that the second section is out of plane of the first section.

Accordingly, in certain variations, a portion or the entire first section of the bone plate may be angled with respect to a portion or the entire second section of the bone plate, wherein the angle may range from about 1° to about 90°, such as from about 5° to about 45°, for instance, from about 7.5° to about 30°, including from about 10° to about 20°, such about as 15°. In this manner, the bone plate may have a "T" shaped configuration and may be configured so as to be associated with another bone plate, and further may be configured so as to contact a bone surface wherein the bone surface has an angled or curved morphology with respect to the plane of the other bone plate.

The proximal and/or distal portions of the second section of the bone plate may be curved or angled with respect to the intercalating portion and/or each other. For instance, the second section may include a curvature, which curvature may span a portion or the entire length of the second section. In certain embodiments, one or more of the portions of the second section of the secondary bone plate are angled with respect to each other, wherein the angle may range from about 1° to about 90°, such as from about 5° to about 45°, for instance, from about 7.5° to about 30°, including from about 10° to about 20°, such about as 15°.

One or more regions of the primary and/or secondary bone plates may be configured for contacting and being attached to a bone portion. Hence, in certain embodiments, the primary or secondary bone plate includes one or more apertures or openings, such as an opening that spans the thickness of the bone plate and extends between a bottom or bone contacting surface and a top surface thereof. The opening may be of any suitable configuration, and in some embodiments, the opening is adapted to receive a securing member or fastener so as to attach the bone plate to a bone portion. One or more openings herein may include a sleeve portion that extends through the opening and may be configured for receiving a locking screw therein. Accordingly, in certain embodiments, the primary and/or secondary bone plate includes one or more, e.g., a plurality of openings, wherein the openings are positioned in a distal, intercalating, and/or proximal portion of the primary and/or secondary bone plate.

For instance, one or more of a proximal, intercalating, or distal region and/or engagement element of the primary and/or secondary bone plate may include one or more openings. For example, the proximal body portion of the primary bone plate may include an opening that is configured for receiving a fastener, such as a fastener that is adapted so as to attach the primary bone plate to a bone portion, e.g., a first bone portion. In certain variations, an intercalating or a proximal portion of the primary bone plate is configured for being attached to a bone portion and thus may include one or more openings. For instance, the engagement element of the primary or secondary bone plate may include an opening positioned in the distal or proximal portion of the bone plate that is adapted for receiving a fastener, such as a fastener that may be inserted through the opening and functions to couple the primary bone plate to an additional, secondary bone plate, and/or a bone portion, e.g., a second bone portion.

This opening, as well as any other opening included in the bone plate system, may be of any suitable configuration. For instance, the opening may be round, e.g., circular or semi-circular, triangular, square, ovoid, arced, elliptical, or the like. For instance, in certain embodiments, the opening is circular and in certain embodiments the opening is semi-circular, arced, or ovoid. In certain embodiments, two or more openings are included and positioned at the distal portion of the primary and/or the proximal portion of the secondary bone plate. For instance, in certain embodiments, one or more openings are circular and an additional one or more openings is semi-circular or arced or ovoid. Where an opening is circular, it may have a diameter that ranges from about 0.5 mm to about 5 mm, such as from about 1 mm to about 4 mm, including about 2 mm or about 2.5 mm to about 3 mm. Where an opening is ovoid, it may have a width that ranges from about 0.5 mm to about 5 mm, such as from about 1 mm to about 4 mm, including about 2 mm or about 2.5 mm to about 3 mm; and it may have a length that ranges from about 2 mm to about 15 mm, such as from about 5 mm to about 9 or about 10 mm, including about 7 mm to about 8 mm.

In certain variations, the distal body portion of the secondary bone plate may include an opening that is configured for receiving a fastener, such as a fastener that is adapted so as to attach the secondary bone plate to a bone portion, e.g., a third bone portion. In certain variations, one or more openings, as described herein, include threading such as threading that corresponds to threading positioned on a fastener. In at least this manner, a fastener may be inserted into and through the opening by rotating the fastener in such a manner that the threads of the fastener align with the corresponding threads of the opening. In certain embodiments, one or more openings do not include threading such that the fastener may be inserted there through without threading the fastener into the opening.

As can be seen above, a subject bone plate with flange member, and/or bone plate system, may have a variety of configurations adapted to capture fracture fragments, which may be distal to a primary bone portion and/or a fracture therein, so as to reduce the fragmented portion(s) in correct alignment with another, e.g., primary, bone portion and thereby stabilize the fracture portions and facilitate the appropriate healing of the fractured and/or fragmented bone. To that extent, the bone plate(s) of the present bone plate system may include a multiplicity of elements, for instance, engagement elements, which may include tab and tab receiving portions of varying angels; as well as openings, such as securing apertures of differing configurations that are adapted to receive and align a fastener at varying orientations to the bone plate and/or underlying bone. In this manner, the bone plates and systems set forth herein provide a flexible interface for reducing and stabilizing fractures, including peri-articular fractures that are out of plane from a main, primary bone shaft.

DESCRIPTION OF THE FIGURES

As summarized above, aspects of the disclosure include a bone plate with an extended body that includes one or more flange members positioned below a bottom surface of the extended body. The bone plate with flange member may be used alone or in conjunction with another bone plate so as to form a bone plate system. Due to the adaptability of the present bone plate, and/or bone plate system, to differing bone morphologies, the bone plate and system are well suited for reducing, aligning, and/or fixing comminuted fractures, for instance, wherein the fracture includes a fragmented bone portion, such as a fragmented bone portion that is located distal to a primary bone shaft portion and/or positioned at an angle thereto. For example, the bone plate with flange member and/or bone plate system may be configured so as to reduce, align, and/or fix one or more fragmented bone portions, wherein the fragmented bone portions may be distal to and/or out of plane from one another, so as to treat a bone fracture, such as bone fracture positioned at a diaphyseal, peri-articular, metaphyseal bone portion in an upper or lower extremity.

Accordingly, for the purpose of reducing and/or stabilizing a bone fracture a single bone plate of the disclosure may be provided. Alternatively, a bone plate system may be provided, wherein the system includes a plurality of bone plates that are configured for being both attached to one or more bone portions and coupled to one another. At least one of the bone plate(s) provided includes a flange member, which flange member is adapted to reduce, fix and/or stabilize one or more fractured bone portions in correct anatomical and/or healing alignment for the treatment of the bone fracture. Reference will now be made in detail to various embodiments of the disclosure, which are illustrated in the accompanying figures.

Referring now to FIG. 1, a primary bone plate 10 of the present disclosure is set forth. FIG. 1A provides a perspective top view of the primary bone plate 10. FIG. 1B provides a perspective bottom view of the primary bone plate 10 of FIG. 1A. FIG. 1C provides a perspective bottom front view of the bone plate of FIG. 1A. FIG. 1D provides a perspective top front view of the bone plate of FIG. 1A.

The primary bone plate 10 includes an extended, elongated body 20. The elongated body 20 includes a proximal portion 23 with a proximal end 22, a distal portion 25 with a distal end 26, and an intercalating portion 24 interposed between the proximal and distal portions. The elongated body 20 additionally includes a top surface 29 and a bottom or bone contacting surface 21.

A top surface 29a of the proximal portion 23 is substantially planar. Additionally, a top surface 29b of the distal portion 25 is also planar. However, as illustrated, a first plane 1 corresponding to top surface 29a of the proximal portion 23 transects a second plane 2 corresponding to a top surface 29b of the distal portion 25. Accordingly, as depicted, the distal portion 25 is out of plane or angled with respect to the primary plane 1 of the proximal portion 23.

The primary bone plate 10 additionally includes a first side 27 and a second side 28. As can be seen with reference to FIG. 1B, the bottom surface 21a of the proximal portion 23 includes a curvature between sides 27 and 28, giving the proximal portion a concaved configuration, such as a configuration that is adapted to fit a curved contour of a bone to which the bone plate 10 is to be attached.

The distal portion 25 includes a flange member 40, extending below the bottom surface 21b of the bone plate 10, and a flange member aperture 50, which aperture is positioned in a central portion of the distal portion 25. Accordingly, as depicted, the flange member 40 is a cut out portion that has been formed from cutting a segment of the distal portion 25 and folding the segment in such a manner that it includes a portion 44 that is displaced below the bottom surface 21 of the distal portion 25 and includes a portion that extends in a direction that is parallel to the secondary plane 2. Because the flange member 40 is formed from the elongated body 20 of the bone plate 10, displacement of the portion 44 of the flange member below the bottom surface 21 leaves the flange member extending from the flange member aperture 50 in the distal portion 25 of the elongated body of the bone plate.

The flange member 40, therefore, includes two portions or segments, a first portion, such as a connector 42, and an extended body portion 44. The connector 42 is configured as a post element that extends downwards, away from a bottom surface 21b of the distal portion 25, such that a plane 3 defined by a surface of the connector 42 transects primary plane 2 of the top surface 29b of the distal portion 25. Accordingly, as depicted the connector 42 is positioned perpendicular to the bottom surface 21b of the distal portion 25 and extends downward there from (this angle may vary as described above). The extended body portion 44 includes a top surface, or bone engaging surface 46 and a bottom surface 48. The top surface 46 corresponds to a plane 4 which plane transects plane 3 of the connector 42 at a relatively 90° angle (which angle may vary as described above) and is substantially parallel to plane 1 of the top surface 29b of the distal portion 25. Thus, as depicted, the extended body 44 of the flange member 40, is roughly perpendicular to the connector 42, parallel to the top surface 29b of the distal portion 25, and displaced there from by a distance equivalent to the length of the connector 42. Consequently, the flange member may be considered to have an L-shape, which gives the distal portion 25, as a whole, the configuration of a can or bottle opener.

The elongated body 20 of the primary bone plate 10 additionally includes a plurality of openings, 15a, 15b, and 15c, positioned in the proximal portion 23 of the elongated body 20. The elongated body 20 additionally includes a plurality of openings, collectively 15e, positioned in the distal portion 25 of the elongated body 20. The elongated body 20 also includes an opening 15d positioned in the intercalating portion 24 of the elongated body. The openings extend between the bone contacting surface 21 and the top surface 29 of the elongated body. As depicted, openings 15a, 15b, 15c, and 15e are recessed, round or circular, and opening 15d is longitudinal and oval. It is to be understood that fewer or more openings than illustrated may be included.

Figure 1B:
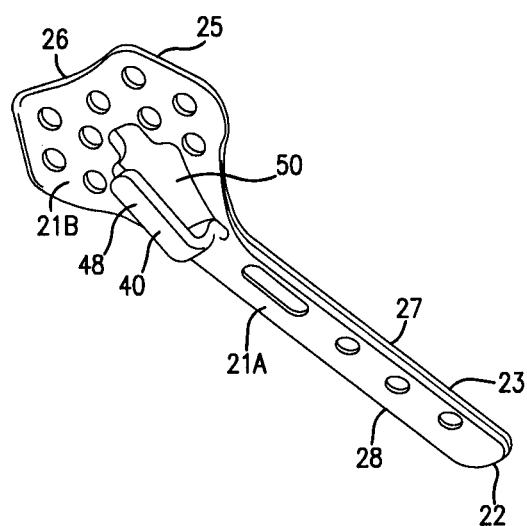
FIG. 1B provides a perspective bottom view of the primary bone plate of FIG. 1A.

FIGS. 1A and 1B depicts a primary bone plate 10 that includes an elongate body 20 and a flange member 40. The flange member 40 is associated and continuous with a bottom surface 21b of the elongate body 20. The flange member includes a connector element 42 and an extended body portion 44, which extended body portion 44 extends longitudinally parallel to the bottom surface 21 of the elongated body 20. The extended body portion 44 of the flange member 40 may be configured so as to be inserted within an opening within a bone portion, such as a fragmented and/or displaced bone portion in need of reduction. See for instance, FIG. 2.

Figure 1C:
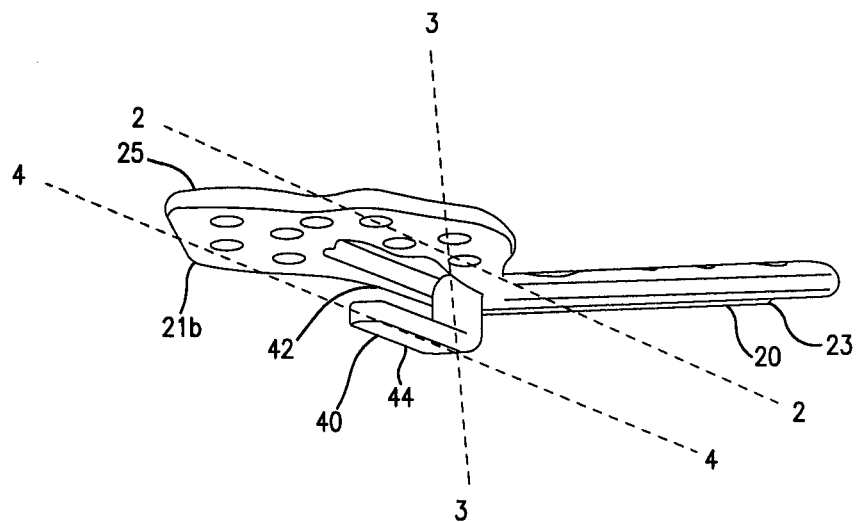
FIG. 1C provides a perspective bottom front view of the bone plate of FIG. 1A.
Figure 1D:
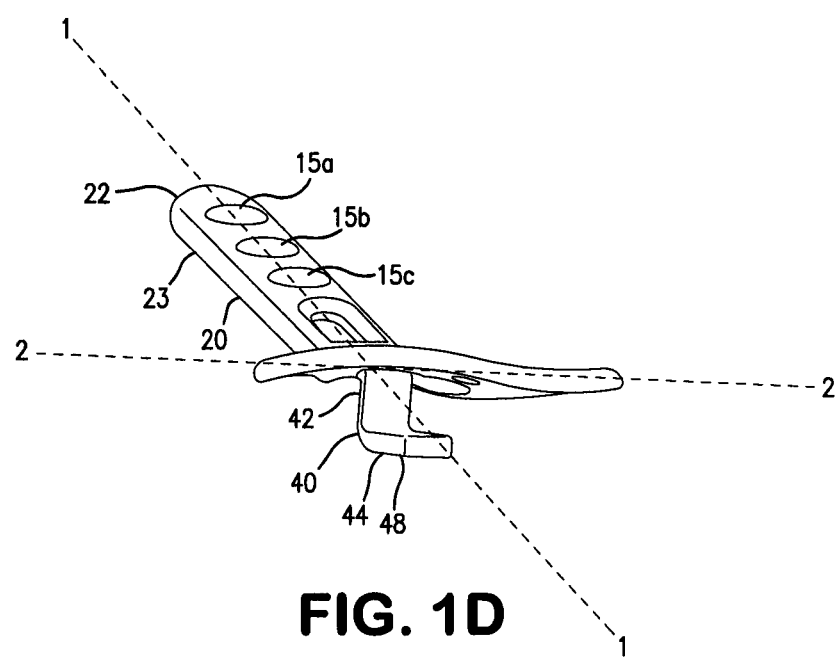
FIG. 1D provides a perspective top front view of the bone plate of FIG. 1A.

FIGS. 1C and 1D depict alternative views of the bone plate 10 of FIG. 1A. As can be seen with reference to FIG. 1C, a plane 4 defined by a top surface of the extended body portion 44 of the flange member 40 transects a plane 3, defined by a surface of the connector 42, at a 90°, and is parallel to a plane 2 defined by the top surface 29b of the distal portion 22 of the elongated body 20 of the bone plate 10. As can be seen with reference to FIG. 1D, the extended body portion 44 of the flange member 40 is displaced from the bottom surface 21 of the bone plate 10 by a distance that is equivalent to the length of the connector element 42.

Figure 2A:
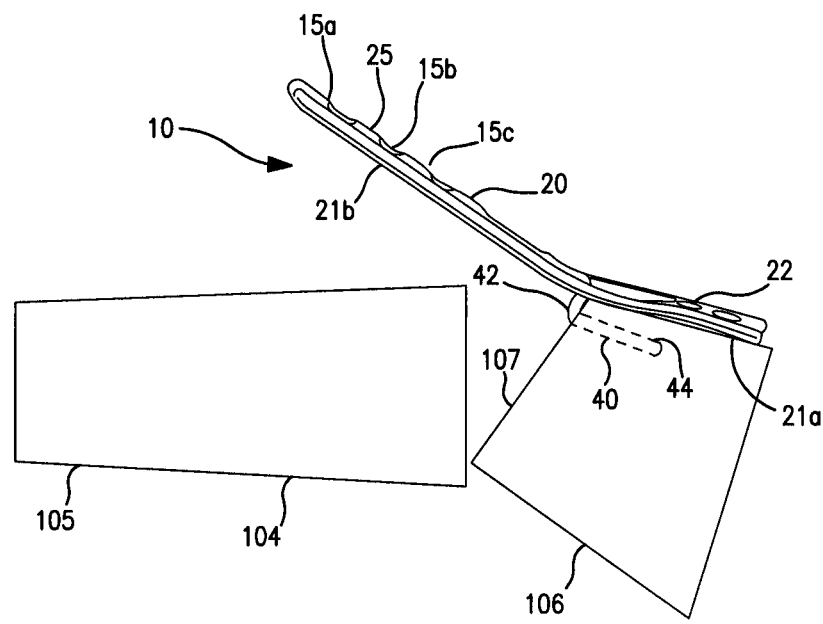
FIGS. 2A and 2B provide a side view of the primary bone plate of FIG. 1A as the bone plate would be used to reduce a fractured and displaced distal bone portion of a long bone.

Referring now to FIG. 2, the primary bone plate 10 of FIG. 1A is set forth as the bone plate 10 would be used to reduce a fractured and displaced distal bone portion 106 of long bone 104. As can be seen with reference to FIG. 2A the flange member 40 of primary bone plate 10 is inserted into an opening 107 in the distal fractured bone portion 106 of long bone 104. The bone plate 10 may be manipulated in relation to the proximal bone fraction portion 105 and distal fraction portion 106 in such a manner that the extended body portion 44 of the flange member 40 is inserted into the cavity 107 of the bone portion 106, and a bottom surface 21b of the distal portion 25 of the bone plate 10 comes into contact with an extramedullary surface of the fractured bone portion 106.

The flange member 40 may be configured so as to contact an intramedullary bone portion of fractured bone portion 106 in such a manner that the bone portion 106 is sandwiched between the bottom surface 21b of the distal portion 25 of the elongated body 20 and the top surface of the extended body portion 44 of the flange member 40. Accordingly, the extramedullary bone contacting surface 21b of the distal portion 25 may be referenced as a first bone engaging surface of the bone plate 10, and the intramdullary bone facing or contacting surface 46 of the extended body 44 of the flange member 40 may be referenced as a second bone engaging surface of the bone plate 10.

Figure 2B:
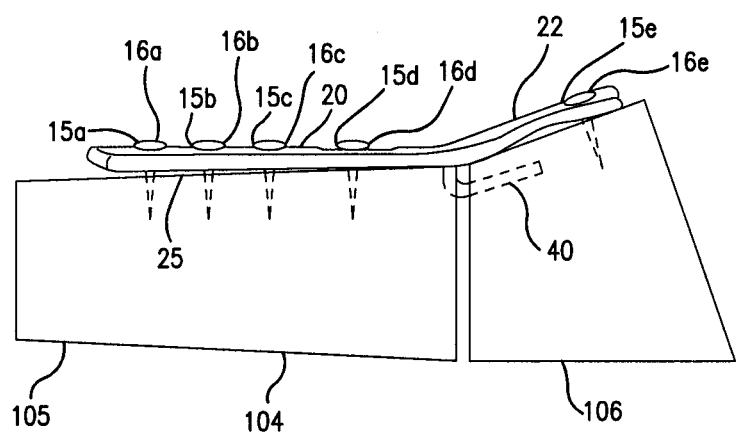

As can be seen with reference to FIG. 2B, once inserted, the flange member 40 can be used to reduce and align the distal fractured bone portion 106 in correct anatomical and/or healing alignment with proximal fractured bone portion 105. When the two bone portions are aligned, fasteners 16a-e may be inserted into openings 15a-e so as to fasten bone plate 10 onto bone portions 105 and 106, so as to treat and heal the fracture in bone 104.

FIG. 2B provides a depiction of the bone plate with flange member as it would be when appropriately positioned so as to reduce, align, and stabilize a bone fracture. As depicted, the bone plate 10 is positioned so that the extended body portion 44 (shown as cut out portion) of the flange member 40 is inserted inside a cavity within the distal bone portion 106. Fasteners collectively depicted as 16f are inserted into openings collectively depicted as 15f so as to attach the distal portion 25 of the bone plate 10 to the distal bone portion 106. In this manner, a portion of the bone fragment 106 will be sandwiched between a top surface 46 of the extended body portion 44 and a bottom surface 21b of the distal portion 25 of the bone plate 10. The proximal portion 23 of the bone plate 10 may then be used to align the distal bone portion 106 with the proximal bone portion 104. Once aligned, the proximal portion 23 of bone plate 10 may be attached to the proximal bone portion 104 so as to reduce and stabilize the bone fracture of bone 102, as depicted in FIG. 2B.

As described above, an aspect of the disclosure provides for a bone plate system. The bone plate system may be employed to reduce and/or fix one or more bone portions for the treatment of a bone fracture, for example. The bone plate system may include a proximal or primary bone plate and a distal or secondary bone plate, one of which bone plates includes a flange member.

Figure 3A:
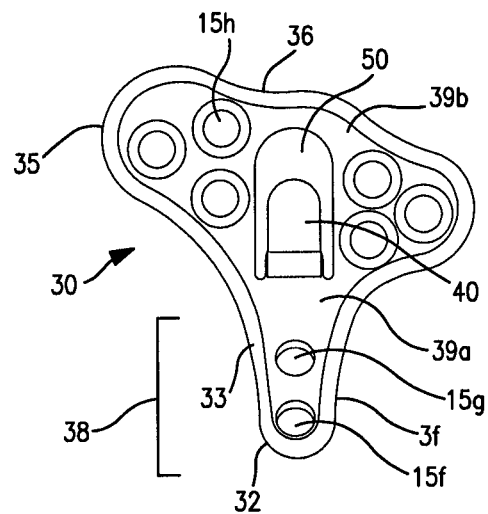
FIG. 3A provides a perspective top view of a secondary bone plate in accordance with the disclosure.
Figure 3B:
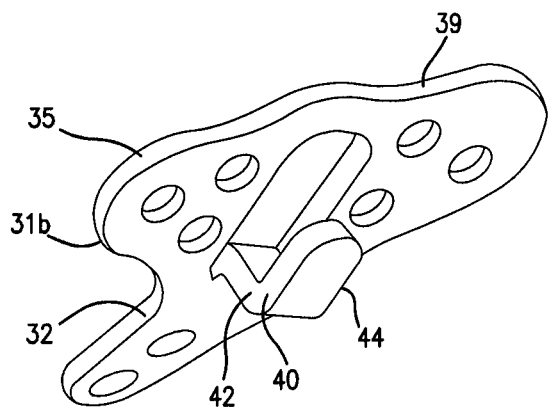
FIG. 3B provides a perspective bottom view of the secondary bone plate of FIG. 3A.
Figure 3C:
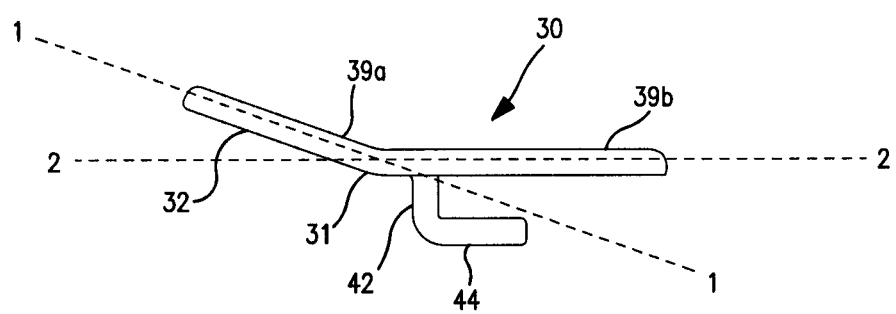
FIG. 3C provides a side view of the bone plate of FIG. 3A.

For instance, FIG. 3 provides a distal or secondary bone plate 30 that comprises one of at least two bone plates of a bone plate system 5 in accordance with the disclosure. FIG. 3A provides a perspective top view of a secondary bone plate 30 in accordance with the disclosure. FIG. 3B provides a perspective bottom view of the secondary bone plate 30 of FIG. 3B. FIG. 3C provides a side view of the bone plate of FIG. 3A.

The secondary bone plate 30 includes an extended body. The extended body includes a proximal portion 33 with a proximal end 32, a distal portion 35 with a distal end 36, and an intercalating portion 34 interposed between the proximal 33 and distal 35 portions. The extended body additionally includes a top surface 39, as illustrated in FIG. 3A, and a bottom or bone contacting surface 31, as illustrated in FIG. 3B.

As illustrated in FIG. 3C, a top surface 39a of the proximal portion 33 is substantially planar. Additionally, a top surface 39b of the distal portion 35 is also planar. However, as depicted, a first plane 1 corresponding to top surface 39a of the proximal portion 32 transects a second plane 2 corresponding to a top surface 39b of the distal portion 35. Accordingly, as depicted, the proximal portion 32 is out of plane or angled with respect to the distal portion 35.

As illustrated in FIG. 3B, the distal portion 35 includes a flange member 40, extending below the bottom surface 31b of the bone plate 30, and a flange member aperture 50, which aperture is positioned in a central portion of the distal portion 35. The flange member 40 includes a connector 42 and an extended body portion 44.

The secondary bone plate 30 includes a plurality of openings, 15f and 15g positioned in the proximal portion 33, and includes a plurality of openings, collectively 15h, positioned in the distal portion 35 of the extended body. The openings extend between the bone contacting surface 31 and the top surface 39 of the extended body. As depicted, the openings are recessed, round or circular. It is to be understood that fewer or more openings than illustrated may be included.

The secondary bone plate 30 additionally includes a bone plate engagement portion 38. Specifically, the proximal portion 33 and the proximal end 32 are configured as a tab insertion member 38, which tab insertion member is configured for being associated with another bone plate, such as a primary bone plate, so as to allow the secondary bone plate to be coupled to the primary bone plate for the reduction of a bone fracture positioned between the two bone plates, as described in greater detail herein below.

Accordingly, as illustrated in FIG. 4, a bone plate system is provided. The bone plate system 5 includes at least a first or primary bone plate 10, which bone plate may be a diaphyseal bone plate, and a secondary bone plate 30, which bone plate may be a peri-articular or juxta-articular bone plate, and wherein the secondary bone plate 30 includes a flange member 40.

As depicted, the primary bone plate 10 is elongated and includes a proximal portion 23 with a proximal end 22, a distal portion 25 with a distal end 26, and an intercalating portion 24 between the distal and proximal portions. The primary bone plate 10 additionally includes a plurality of openings 15a-e. Openings 15a and 15b are circular and positioned in the proximal portion 23 of the primary bone plate 10. Opening 15c is oval and aligned in the longitudinal direction of the intercalating portion 24 of the primary bone plate 20. Openings 15d and 15e are positioned in the distal portion 25 of the primary bone plate 22. Opening 15d is circular and opening 15e is oval and aligned in the transverse direction. The openings 15a-15e extend between the bone contacting surface 21 and the top surface 29, may be recessed, and are configured for receiving a fastener there through. It is to be understood that more or less openings than illustrated.

The secondary bone plate 30 includes an extended body. The extended body includes a proximal portion 33 with a proximal end 32, a distal portion 35 with a distal end 36, and an intercalating portion 34 interposed between the proximal 33 and distal 35 portions. The extended body additionally includes a top surface 39 and a bottom or bone contacting surface 31. The distal portion 35 includes a flange member 40, extending below the bottom surface 31 of the bone plate 30, and a flange member aperture 50, which aperture is positioned in a central portion of the distal portion 35. The flange member 40 includes a connector 42 and an extended body portion 44. The secondary bone plate 30 additionally includes a plurality of openings, 15f and 15g positioned in the proximal portion 33, and includes a plurality of openings, collectively 15h, positioned in the distal portion 35 of the extended body.

The primary bone plate 10 and the secondary bone plate with flange member 40 may be configured for being attached to one or more bone portions, such as two bone portions separated by a fracture site, and may be adapted to be coupled together with one another so as to reduce, fix and/or stabilize, for example, the one or more bone portions in healing alignment for the treatment of a bone fracture.

Figure 4A:
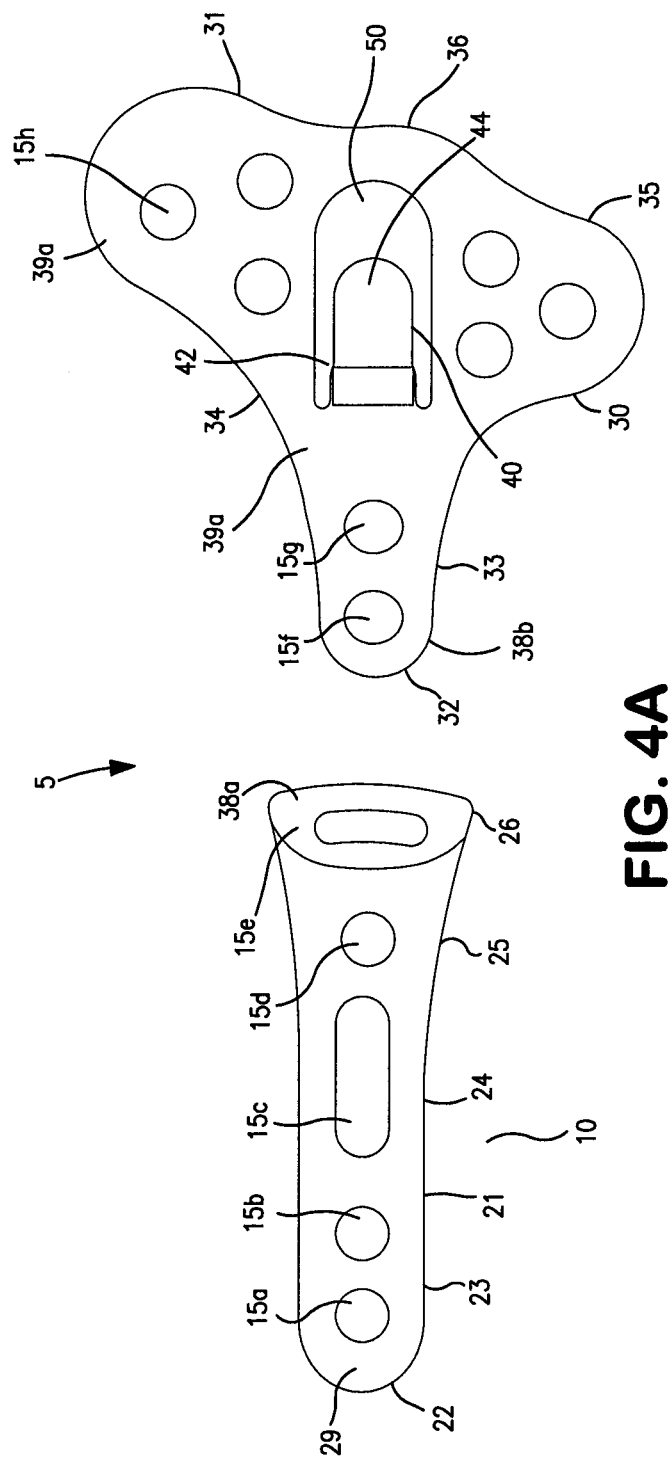
FIG. 4A illustrates a top view of the bone plate system prior to the coupling of the bone plates.

Accordingly, as can be seen with reference to FIG. 4A, the distal portion 25 of the primary bone plate 10 is configured for being coupled to the proximal portion 33 of the secondary bone plate 30. Accordingly, the distal portion 25 of the primary bone plate 10 includes a secondary bone plate engagement portion 38a, which engagement portion is configured as a cut-out or recessed and hooded slot portion within the distal portion 25 of the primary bone plate 10. As depicted, the recessed portion is tapered and configured so as to form a slot. Further, the proximal portion 32 of the secondary bone plate 30 includes a primary bone plate engagement portion 38b, which engagement portion is configured as an extended or tab portion positioned at the proximal portion 33 of the secondary bone plate 30, which tab portion is configured for being received within the slot portion of primary bone plate 10.

Figure 4B:
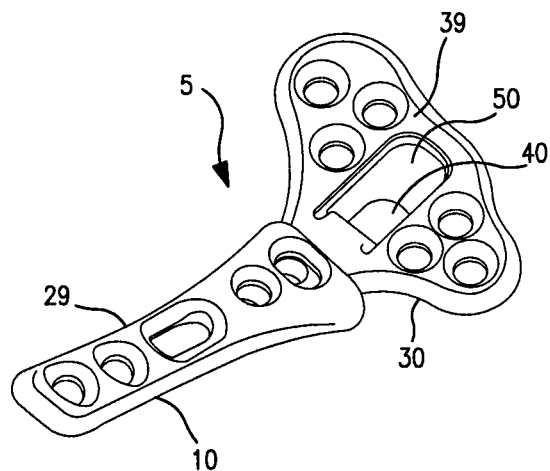
FIG. 4B illustrates a top view of the bone plate system of FIG. 4A after the coupling of the bone plates.
Figure 4C:
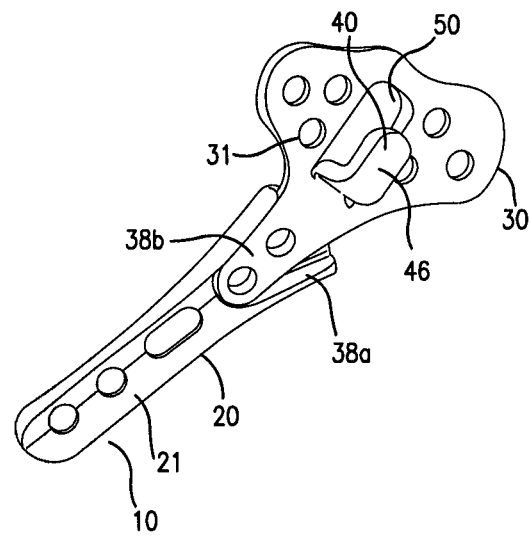
FIG. 4C illustrates a bottom view of the bone plate system of FIG. 4B after the coupling of the bone plates.
Figure 4D:
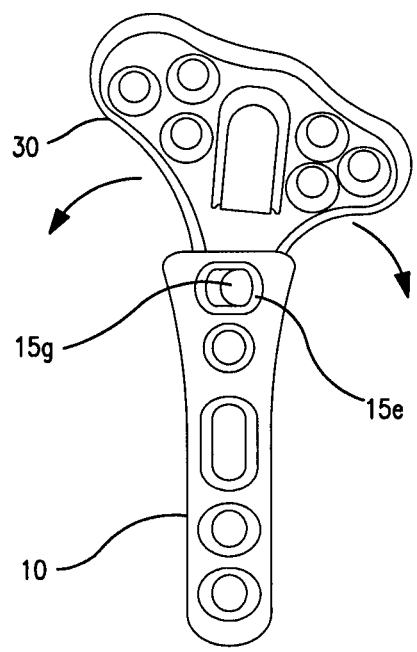
FIGS. 4D and 4E illustrate how the primary and secondary plates may be adjusted in the lateral direction.
Figure 4E:
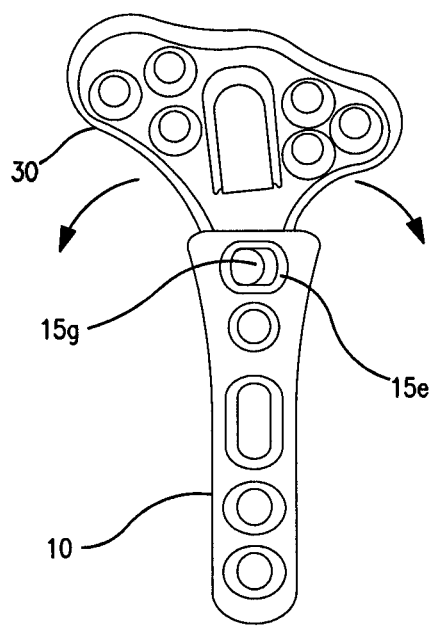

FIG. 4A illustrates a top view of the bone plate system 5 prior to the coupling of the bone plates, e.g., prior to insertion of tab member 38b into tab receiving member 38a. FIG. 4B illustrates a top view of the bone plate system of FIG. 4A after the coupling of the bone plates, e.g., after insertion of tab member 38b into tab receiving member 38a. As can be seen with reference to FIG. 4B, the top surface 39b of the distal portion 35 is angled with respect to both the top surface 39a of the proximal portion 33 of the secondary bone plate 30 and the top surface 29 of the bone primary bone plate 20. As described above, this angle may be configured such that it allows the bone plate, e.g., a distal portion thereof, to conform to any suitable bone morphology to which the bone plate is to be attached. In this manner, the two bone plates may be coupled together in plane with one another, and the distal portion 35 of the secondary bone plate 30 may be angled thereto. FIG. 4C illustrates a bottom view of the bone plate system of FIG. 4B after the coupling of the bone plates, e.g., after insertion of tab member 38b into tab receiving member 38a. As can be seen with reference to FIG. 4C, the elongated body 20 of the primary bone plate 10 is concave. FIGS. 4D and 4E illustrate how the primary and secondary plates may be adjusted in the lateral direction prior to insertion of a securing fastener into transverse oval opening 15e. In this manner, the two bone plates may be adjusted after coupling together so as to achieve an appropriate anatomical alignment prior to being completely secured together.

Figure 5A:
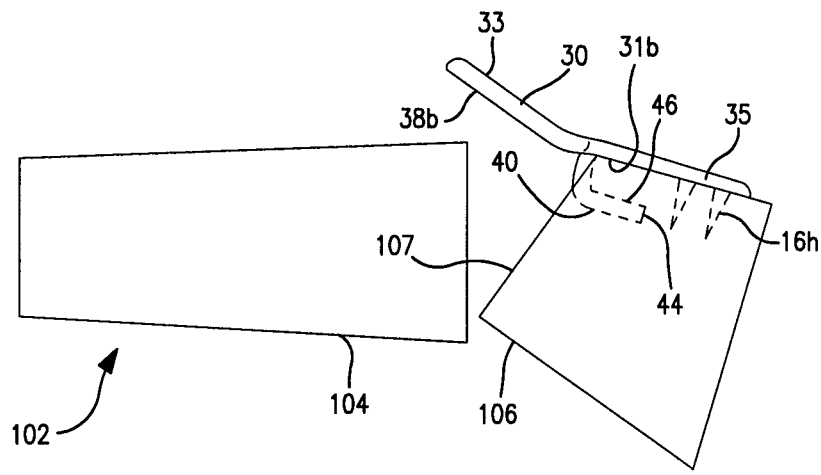
FIG. 5A, provides a side view of a secondary bone plate of the bone plate system of FIG. 4 as it would attached to a bone fracture.

As illustrated in FIG. 5A, the bone plate system 5 of FIG. 4 is provided as it would be used to align a bone fracture. The system 5 includes a primary bone plate 10 and a secondary bone plate 30. As depicted in FIG. 5A, the secondary bone plate 30 is positioned so that the extended body portion 44 of the flange member 40 is inserted inside a cavity 107 within the distal bone portion 106. Fasteners collectively depicted as 16h are inserted into openings in the distal portion 35 of the bone plate 30 so as to attach the distal portion 35 to the distal bone portion 106. In this manner, a portion of the bone fragment 106 will be sandwiched between a top surface 46 of the extended body portion 44 and a bottom surface 31b of the distal portion 25 of the bone plate 10.

Figure 5B:
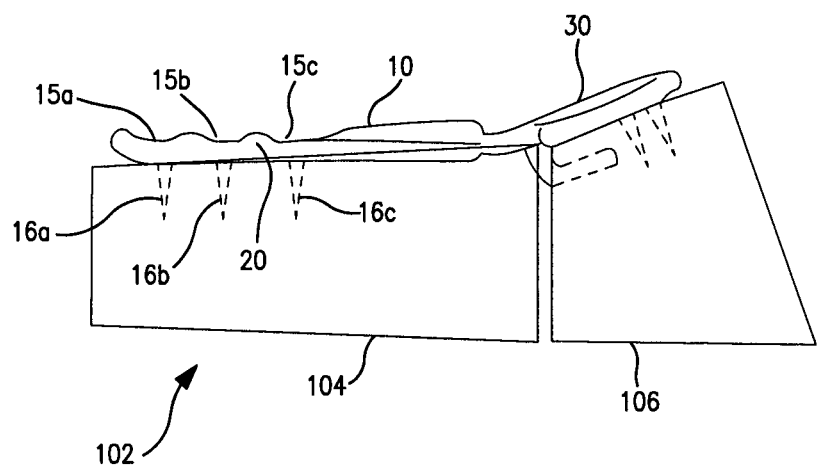
FIG. 5B provides a side view of a primary and a secondary bone plate system of FIG. 4 as they would be used of reduce a fracture portion.

As depicted in FIG. 5B, the primary bone plate 10 is associated with the bone portion 104 and attached thereto by insertion of fasteners 16a-c into openings 15a-c. The proximal portion 33 of the bone plate 10 may then be used to align the distal bone portion 106 with the proximal bone portion 104. Specifically, once inserted into and attached onto the fractured and displaced distal bone portion 106, the bone plate 30 may be used to reduce and align the fractured bone portion 106 in correct anatomical and/or healing alignment with proximally positioned bone portion 104. When the two bone portions 106 and 104 are aligned, the angled tab insertion portion 38b of the secondary bone plate 30 may be inserted into the hooded tab receiving portion 38a of the primary bone plate 10 so as to reduce and stabilize the bone fracture of bone 102.

Figure 5C:
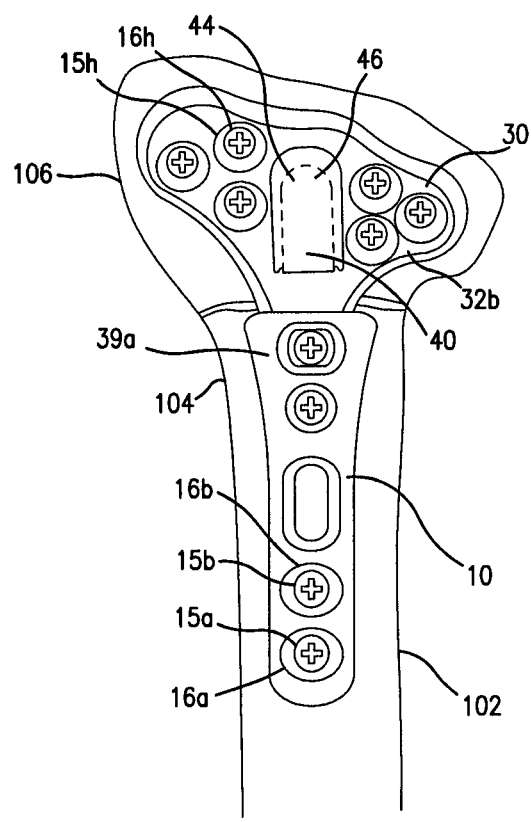
FIG. 5C provides a depiction of the bone plate system of FIG. 5B as it would be when appropriately positioned so as to reduce, align, and stabilize a bone fracture.

FIG. 5C provides a depiction of the bone plate system of FIG. 5, which bone plate system includes a primary bone plate 10, as described above, and a secondary bone plate with flange member, as it would be when appropriately positioned so as to reduce, align, and stabilize a bone fracture. As depicted, the secondary bone plate 30 is positioned so that the extended body portion 44 (shown as cut out portion) of the flange member 40 is inserted inside a cavity within the distal bone portion 106. Fasteners collectively depicted as 16h are inserted into openings collectively depicted as 15h so as to attach the distal portion 35 of the bone plate 30 to the distal bone portion 106. In this manner, a portion of the bone fragment 106 will be sandwiched between a top surface 46 of the extended body portion 44 and a bottom surface 31b of the distal portion 35 of the bone plate 30. The primary bone plate 10 is attached to bone portion 104 by insertion of fasteners 16a-b into openings 15a-b. The angled tab insertion portion (not shown) of the secondary bone plate 30 is inserted into the hooded tab receiving portion 39a of the primary bone plate 10 so as to reduce and stabilize the bone fracture of bone.

As illustrated in FIG. 5, the distal fractured bone portion 106 includes a curved and/or angled morphology. Accordingly, the primary and secondary bone plates 10 and 30 are adapted such that their configuration conforms to the morphology of the bone portions to which the bone plates are to be attached. Hence, the primary and secondary bone plates 10 and 30 are configured such that the coupling of the tab insertion portion 38b of the secondary bone plate 30 into the hooded tab receiving portion 38a of the primary bone plate 20 produces a natural reduction of the two bone portions. Specifically, the primary and secondary bone plates 10 and 30 are configured such that their coupling recapitulates the angle of the non-planar bone portion 106.

Thus, the configuration(s) of the primary and secondary bone plates 10 and 30 are such that the two bone plates may be coupled with one another so as to correctly reduce, align, stabilize, and/or restore the two bone portions 104 and 106 to a position that at least approximates their natural position and thereby treats the bone fracture in long bone 102. Accordingly, given the adaptable configurations of the various elements of the bone plate system disclosed herein, the present system is capable of reducing and fixing a bone fracture.

In one aspect, the subject matter described herein is directed to methods of using such bone plate systems, as described herein above, so as to align, reduce and/or fix one or more fractured bone portions for the treatment thereof, for example. Accordingly, in certain embodiments, a general method is provided for reducing a bone fracture, wherein the method includes the steps of providing a first and a second bone plate, wherein the first and second bone plates are configured for being coupled to one another in an angled relationship, attaching the first bone plate to a first bone portion, attaching the second bone plate to a second bone portion, and coupling the first and second bone plates together so as to reduce the fractured bone portions.

The bone plates may be attached to their respective bone portions in any suitable order. For instance, the primary bone plate may be attached to a first bone portion prior to the attachment of the secondary bone plate to a second bone portion or vice-versa. However, regardless of the order of the attachment of the primary and secondary plates, the secondary bone plate may be attached to a distal and/or fragmented bone portion and used as a lever so as to obtain correct anatomical alignment.

For example, the secondary bone plate may be applied to a distal bone fragment. The application of the secondary bone plate to the distal bone fragment may, but need not, involve the use of a K-wire which may be inserted through an opening in the secondary bone plate, for instance, in the distal portion thereof, so as to be used as a guide to insure correct alignment of the secondary bone plate to the distal fractured bone portion. Accordingly, the K-wire to be applied may be drilled parallel to an articular surface, such as in the lateral plane of the bone fragment. The secondary plate may then be slid over the K-wire and down to the surface of the distal bone fragment. Once contacted and correctly positioned with respect to the distal bone fragment, the secondary bone plate may be attached thereto by the insertion of one or more fasteners, e.g., pegs, through openings in the secondary bone plate. K-wire may also be used to perform this function in addition or substitution for the referenced pegs.

If the primary plate has not heretofore been attached to the primary bone portion it may then be attached to its respective bone portion, for instance, in the manner described above with respect to the secondary bone plate. Once both the primary and secondary bone plates are attached to their respective bone portions, the secondary bone plate may be used, like a joystick, so as to align the bone plate engagement element of the secondary bone plate, with the bone plate engagement element of the primary bone plate in a manner sufficient to allow the primary and secondary bone plates to be coupled together. It is to be noted that the primary and secondary bone plates are not only specifically designed, as described above, to conform to the morphology of the bone portions to which they are attached, but are also designed such that when the primary and secondary bone plates are attached to their respective bone portions, the coupling of the primary and secondary bone plates to one another results in the alignment and proper reduction of the respective bone portions such that when the primary and secondary bone plates are attached to one another the fractured bone portions are stabilized in an alignment that approximates the normal anatomical alignment that the bone was in prior to the fracture and therefore promotes correct and rapid healing, with minimal adverse effects.

As certain changes may be made without departing from the scope of the present subject matter described herein, it is intended that all matter contained in the above description or shown in the accompanying drawings be interpreted as illustrative and not in a literal sense (and thus, not limiting). Practitioners of the art will realize that the method, device and system configurations depicted and described herein are examples of multiple possible system configurations that fall within the scope of the current subject matter described herein.

While the subject matter described herein has been described with reference to the specific embodiments thereof, it should be understood by those skilled in the art that various changes may be made and equivalents may be substituted without departing from the true spirit and scope of the subject matter described herein. In addition, many modifications may be made to adapt a particular situation, material, composition of matter, process, process step or steps, to the objective and scope of the subject matter described herein. All such modifications are intended to be within the scope of the claims appended hereto.

Throughout this application, various publications, patents and published patent applications may be cited. The disclosures of these publications, patents and published patent applications referenced in this application are hereby incorporated by reference in their entirety into the present disclosure. Citation herein by the Applicant of a publication, published patent application, or patent is not an admission by the Applicant of said publication, published patent application, or patent as prior art. Accordingly, all publications and patents cited in this specification are herein incorporated by reference as if each individual publication or patent were specifically and individually indicated to be incorporated by reference.

What is claimed is:

1. A bone plate comprising:
a bone engaging plate segment including a proximal end and a distal end spaced apart from the proximal end by a length of the plate segment, the plate segment also including a first side extending along the length of the plate segment and a second side spaced apart from the first side and extending along the length of the plate segment, a top surface of the plate segment extending from the proximal end to the distal end and from the first side to the second side, a bottom surface of the plate segment extending from the proximal end to the distal end and from the first side to the second side, the bottom surface being a bone contacting surface, a proximal portion of the bottom surface curving upwardly between the first side and the second side to form a concave bottom surface configuration at the proximal portion of the plate segment when viewed from the proximal end, such that the concave bottom surface configuration is adapted to fit a curved contour of a bone, a flange aperture formed in a distal portion of the plate segment between the proximal and distal ends and between the first and second sides, the flange aperture being defined by a closed boundary and extending through the plate segment from the top surface to the bottom surface, a plurality of securing apertures configured for receiving securing elements to affix the bone plate to one or more bone portions and extending through the plate segment from the top surface to the bottom surface of the plate segment, at least a first securing through aperture of the plurality of securing apertures being located in the proximal portion between the proximal end of the plate segment and a proximal side of the flange aperture, at least a second securing through aperture of the plurality of securing apertures being located in the distal portion of the plate segment between the distal end of the plate segment and a distal side of the flange aperture; and a flange member being a cut out segment that has been formed from cutting and folding the cut out segment in the distal portion of the plate segment so as to form a connector and an intramedullary bone engaging stabilization member, the connector extending from the proximal side of the flange aperture downwardly below the bottom surface of the plate segment in a direction being substantially perpendicular a primary plane defined by the bottom surface of the plate segment at the distal portion and coupling the intramedullary bone engaging stabilization member to the plate segment, the intramedullary bone engaging stabilization member extending away from the connector toward the distal end of the plate segment below the bottom surface of the plate segment along a secondary plane being substantially parallel to the primary plane of the plate segment at the distal portion and dimensioned to be substantially within the flange aperture dimensions such the intramedullary bone engaging stabilization member is surrounded by the flange aperture.

* * * * *